United States Patent
Ball et al.

(10) Patent No.: US 6,776,799 B2
(45) Date of Patent: Aug. 17, 2004

(54) METHOD AND APPARATUS FOR REPLICATION OF ANGULAR POSITION OF A HUMERAL HEAD OF A SHOULDER PROSTHESIS

(75) Inventors: Robert J. Ball, Winona Lake, IN (US); Jennifer M. Franklin, Toledo, OH (US)

(73) Assignee: DePuy Products, Inc., Warsaw, IN (US)

( * ) Notice: Subject to any disclaimer, the term of this patent is extended or adjusted under 35 U.S.C. 154(b) by 122 days.

(21) Appl. No.: 10/260,747

(22) Filed: Sep. 30, 2002

(65) Prior Publication Data

US 2004/0064142 A1 Apr. 1, 2004

(51) Int. Cl.[7] .............................. A61F 2/28; A61F 2/54
(52) U.S. Cl. ...................................... 623/19.11; 606/87
(58) Field of Search ........................ 623/19.11–19.14, 623/20.11–20; 606/87–89

(56) References Cited

U.S. PATENT DOCUMENTS

| | | | | |
|---|---|---|---|---|
| 4,893,619 A | * | 1/1990 | Dale et al. ..................... | 606/87 |
| 5,514,143 A | * | 5/1996 | Bonutti et al. ................ | 606/86 |
| 6,168,628 B1 | * | 1/2001 | Huebner ................... | 623/19.11 |
| 6,494,913 B1 | * | 12/2002 | Huebner ................... | 623/19.11 |

\* cited by examiner

*Primary Examiner*—Pedro Philogene
(74) *Attorney, Agent, or Firm*—Maginot Moore & Beck

(57) ABSTRACT

A jig for trialing a head and conjoining portion of a humeral (shoulder) prosthesis and transferring the spatial positioning to a final implant allows a surgeon to adjust humeral head position thereof in three-dimensional space with respect to a humeral component of the humeral prosthesis that has been either previously implanted into a humerus of a patient or not. The jig utilizes a rotatable body such as a sphere that is non-translatable relative to a jig body. A trial implant construct, having a head and neck that is fixed relative to one another (is spatially positioned), is placed in the jig with the neck thereof in contact with the rotatable sphere. As the head is caused to align with markings on the jig and situated flush with the jig, the rotatable sphere replicates the angular position of the neck with respect to a fixed position head. A final implant construct whose components are not fixed relative to one another, is placed in the jig which automatically transfers the spatial positioning of the trial implant construct to the final implant construct.

15 Claims, 16 Drawing Sheets

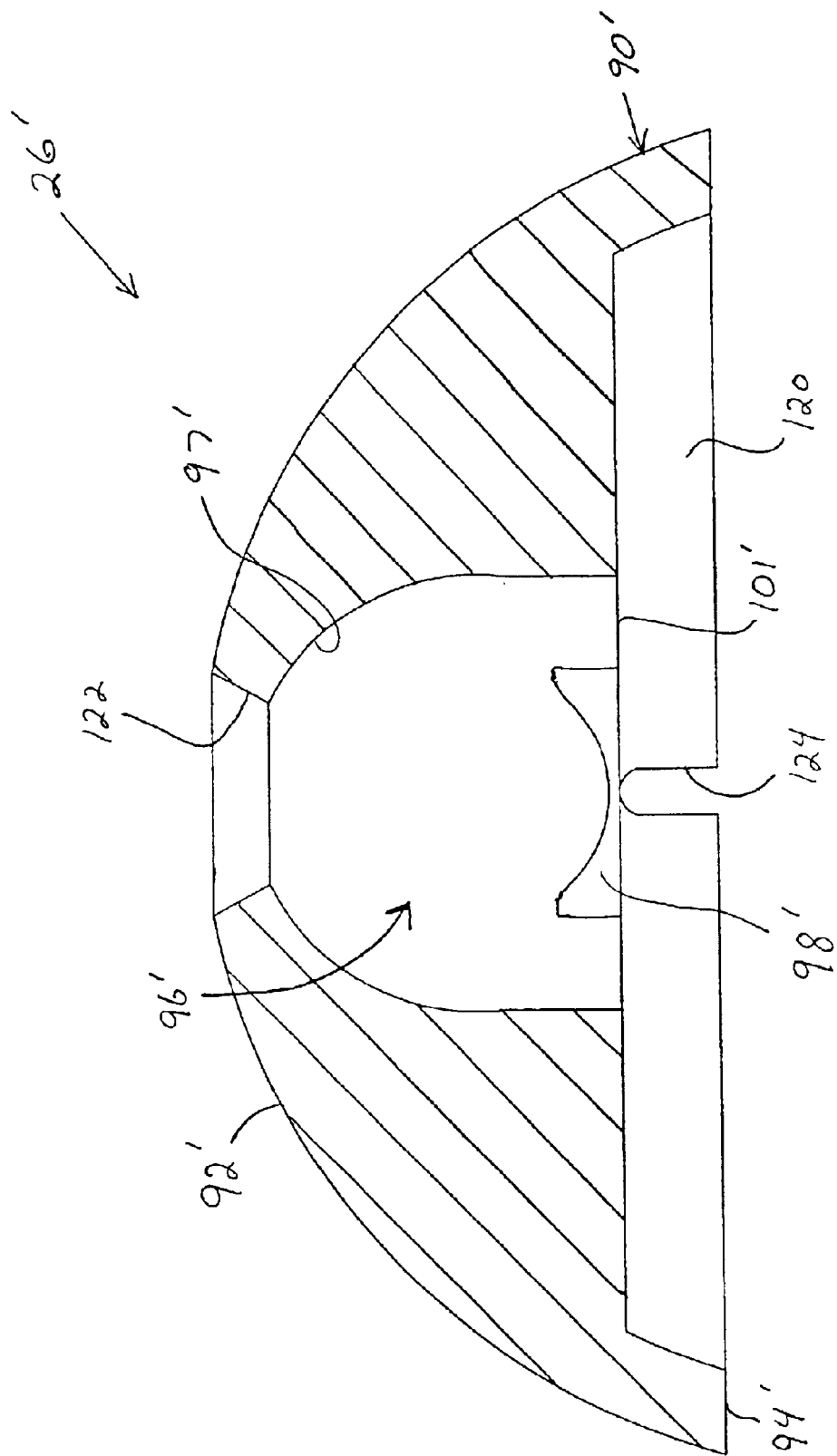

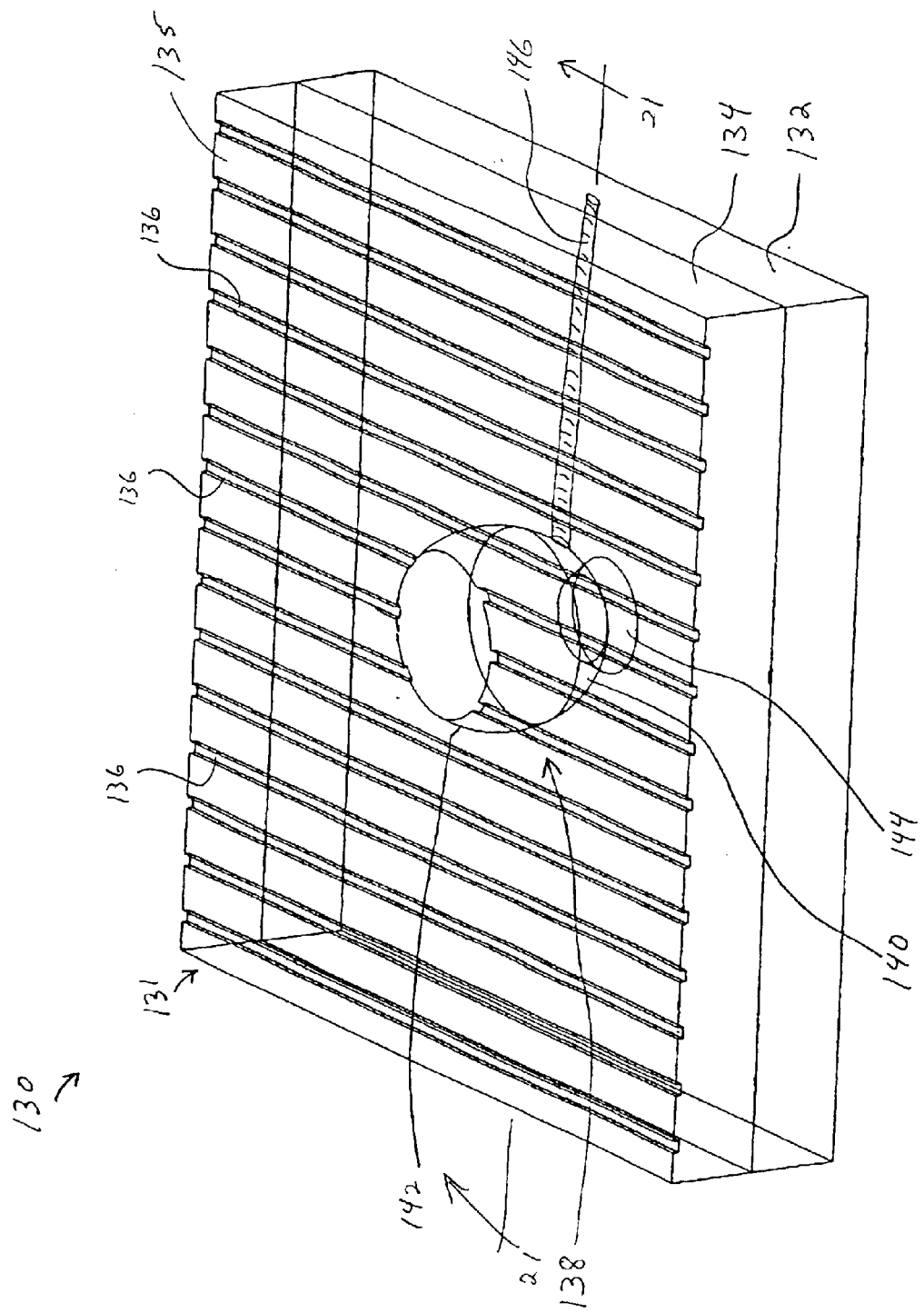

METHOD AND APPARATUS FOR REPLICATION OF ANGULAR POSITION OF A HUMERAL HEAD OF A SHOULDER PROSTHESIS

CROSS-REFERENCE TO RELATED APPLICATIONS

Cross-reference is made to co-pending U.S. Patent Application filed on even date herewith entitled "Shoulder Prosthesis Having a Removable Conjoining Component Coupling a Humeral Component and Humeral Head and Providing Infinitely Adjustable Positioning of an Articular Surface of the Humeral Head" by co-inventors Robert J. Ball and Jeffrey M. Ondrla, and commonly assigned.

BACKGROUND

1. Field of the Invention

The present invention relates to prosthetic devices particularly shoulder prostheses and, more particularly, to a method and apparatus for replication of angular position of a humeral head of a shoulder prosthesis.

2. Background Information

The state of the prosthetic shoulder market has progressed such that a surgeon generally approaches shoulder replacement surgery in one of two strategic ways. One strategic manner is to perform the shoulder replacement surgery in accordance with a manufacturer's shoulder prosthesis or shoulder prosthesis product line. Particularly, a surgeon is provided with instrumentation and technique guidelines for the particular shoulder prosthesis or prosthesis line. The guidelines and/or instrumentation direct or dictate the angle of humeral head resection for the implant (prosthesis). This angle is in relation to the humeral intramedullary (IM) canal and is designed to match an optimum set of angles already present in the prosthetic design.

Another strategic manner is to perform the shoulder replacement surgery in accordance with a patient's anatomy. Particularly, the humeral head is resected according to angles perceived to be "anatomic" in the opinion of the surgeon, not according to angles already present in the prosthetic design. The prosthesis is designed such that the configuration of the prosthesis is intraoperatively adjustable. This allows the prosthesis to be adjustable whereby it can match the boney preparation.

Even with respect to these two divergent manners of surgical strategy, a common problem in shoulder surgery is matching the humeral resection angle to the predetermined angle designed into the prosthesis. This angle may described the angle between a prosthetic collar and the diaphyseal section of the stem. In the case of a collarless stem, the angle may describe the difference between the long axis of the stem and the inferior surface of the prosthetic head. It is considered optimal for fixation and biomechanics if the resected angle and the angle of the prosthesis are identical—thereby allowing intimate contact between the superior surface of resected bone and the inferior surface of the implant.

Moreover, the angular version in which the prosthesis is implanted will have a significant impact on the biomechanics of the prosthetic joint. Currently, most shoulder prosthesis systems on the market dictate the varus/valgus angle of the bone cut. This strategy does not allow the surgeon to easily alter biomechanics after the prosthesis has been trialed, much less implanted.

There are two known products currently marketed that attempt to resolve at least one of the above-noted issues.

First, the Tornier-Aequalis system provides a modular junction within the metaphyseal region of the stem which allows a small block between the stem and humeral head to be interchanged. This block is available in multiple angles, thus allowing the surgeon to select the block that best fits the boney anatomy as resected. This system, however, has two primary weaknesses. First, the use of modular blocks obviously forces the design to only allow angular adjustments in finite increments. Second, the need to adjust the angle through modular blocks forces the surgeon to remove the stem, change out a component, and reset the stem. This presents inconvenience, as well as risk for interfering with resected bone and compromising fixation.

A second product currently marketed as a solution to the problems addressed above is the CenterPulse Anatomica. This product provides a humeral head that is infinitely adjustable in varus/valgus and anterior/posterior angles relative to the stem portion of the prosthesis. This is accomplished through a spherical shaped protrusion on the superior surface of the stem that fits into a spherical recess in the humeral head. These mating surfaces allows the head to be articulated about the stem, thus allowing adjustable positioning of the head. The head can be locked in a position relative to the stem. This solution provides adjustment of the neck-shaft angle as well as being able to affect adjustment of the version through flexibility in the anterior/posterior angle. The locking means, however, is sub-optimal. Particularly, the locking mechanism, requires the turning of a locking screw that has its head facing lateral and inferior, for which there is no access once the stem has been cemented. This eliminates the ability to adjust head position on the fly, and forces a total revision if articular surfaces ever need to be revised. Lastly, the protrusion on the humeral stem even when the humeral head is not in place limits the surgeon's access to the glenoid in preparation for a glenoid replacement.

It should be appreciated that it is desired to have a prosthesis that is intraoperatively adjustable so that it can match the boney preparation. One such prosthesis that has attempted to provide this design feature is made by Sulzer Anatomica. A problem with the Sulzer Anatomica device, however, is replication of the head angular position between the trial prosthesis and the final implant is difficult. In order to alleviate this problem, Sulzer Anatomica provides a jig. The Sulzer Anatomic jig, however, is complicated and cumbersome to use.

Particularly, the Sulzer Anatomica jig has two problems. One problem is that the head position is taken directly from the long axis of the humeral stem. Thus, the trail and implant stems are required to adjust and replicate this position. This means that the Sulzer Anatomica has a large number of components to handle, and the position cannot be adjusted with the stem in vivo. Another problem is that the jig is a quite complicated table-top device. This requires transferring the implant to the back table and setting the implant (stem and head) into the jig. This is technically challenging and time consuming.

With a shoulder prosthesis that allows a surgeon to adjust the angular position of the humeral head (i.e. adjust the articular surface of the humeral head relative to the humeral stem/component and/or bone, a method must be available for trialing the prosthesis. When the trial prosthesis is implanted, several adjustments can be made to set the angular position of the prosthetic head relative to the humeral stem. A means must be available for transferring the settings obtained during the trialing process to the final implant.

What is thus needed in view of the above is a better method for trialing a shoulder prosthesis.

What is further needed in view of the above, is a trialing jig that allows the transfer of settings obtained during the trialing process to the final implant.

What is yet further needed in view of the above, is a quick and easy trialing jig that allows the transfer of setting obtained during the trialing process to the final implant.

SUMMARY

A jig and method of use for trialing a head and conjoining portion of a humeral (shoulder) prosthesis and transferring the spatial positioning to a final implant allows a surgeon to adjust humeral head position thereof in three-dimensional space with respect to a humeral component of the humeral prosthesis that has been either previously implanted into a humerus of a patient or not. The jig utilizes a rotatable body such as a sphere that is non-translatable relative to a jig body. A trial implant construct, having a head and neck that is fixed relative to one another (is spatially positioned), is placed in the jig with the neck thereof in contact with the rotatable sphere. As the head is caused to align with markings on the jig and situated flush with the jig, the rotatable sphere replicates the angular position of the neck with respect to a fixed position head. A final implant construct whose components are not fixed relative to one another, is placed in the jig which automatically transfers the spatial positioning of the trial implant construct to the final implant construct.

According to one embodiment, the jig includes a flat plate in which is positioned a rotatable sphere. The sphere fits into the plate such that the sphere can be rotated about at least two axes that are perpendicular and extend through the center of the sphere, but which cannot translate relative to the plate. A locking means is provided to releasably lock or fix the angular position of the sphere relative to the plate by means of a set screw. The sphere has a hole extending therethrough that receives a neck or extension of a humeral head of the implant construct. The extension from the head is presented into the hole of the sphere. The sphere rotates such that the flat side of the head can rest flat upon the flat plate. The sphere is releasably locked in place and the trial implant construct is removed. A final implant construct is placed in the locked sphere. The head is rotated such that the flat side thereof rests upon the flat plate. Thereafter, the head and neck are locked in position. In this manner, the final implant construct is oriented in the same spatial position as the trial implant construct.

In one form, the subject invention provides a jig for transferring spatial positioning of a humeral head of a first construct relative to a conjoining member of the first construct to a second construct having a humeral head and conjoining member. The jig includes a body defining a flat surface, a cavity within the body, a pivoting member disposed within the cavity, the pivoting member having a configured bore accessible through the body and adapted to freely pivot within the cavity, and locking means situated in the body and adapted to selectively engage the pivoting member to releasably fix a rotational position of the pivoting member. The configured bore is adapted to receive a conjoining member of the first construct and orient the conjoining member relative to a position of the head on the flat surface of the body via pivoting of the pivoting member, the locking means releasably fixing rotational position of the pivoting member during which the first construct is removed and a conjoining member of a second construct is placed therein for alignment according to the fixed rotational position of the pivoting member as a head of the second construct is placed on the position of the head of the first construct on the body, the conjoining member then affixed to the head of the second construct.

In another form, the subject invention provides a jig for transferring spatial orientation of a humeral head to a conjoining member of a first construct to a humeral head and conjoining member of a second construct. The jig includes a body having an upper surface, a spherical cavity, and an opening in the upper surface. A sphere is disposed in the spherical cavity and has a bore configured to receive a neck of a first construct, the sphere being adapted to freely rotate within the spherical cavity and without translation relative to the body. Locking means is situated in the body and is adapted to selectively engage the sphere to releasably fix a rotational position of the sphere. The configured bore is adapted to receive a neck of the first construct and orient the neck relative to a position of the head on the flat surface of the body via rotation of the sphere, the locking means releasably fixing rotational position of the sphere during which the first construct is removed and a neck of a second construct is placed therein for alignment according to the fixed rotational position of the sphere as a head of the second construct is placed on the position of the head of the first construct on the body, the neck then affixed to the head of the second implant construct.

In yet another form, the subject invention provides a method of transferring spatial orientation of a first construct having a humeral head adapted to be releasably affixed to a conjoining member to a second construct having a humeral head adapted to be releasably affixed to a conjoining member. The method includes the steps of: (a) fixing a spatial orientation of a humeral head relative to a conjoining member of a first construct; (b) placing the conjoining member of the first construct into a jig, the jig comprising: a body defining a flat surface; a cavity within the body; a pivoting member disposed within the cavity, the pivoting member having a configured bore and adapted to freely rotate within said cavity; and locking means situated in the body and adapted to selectively engage the pivoting member to releasably fix a rotational position of the pivoting member; wherein the configured bore is adapted to receive a conjoining member of the first construct and orient the conjoining member relative to a position of the head on the flat surface of the body via rotation of the pivoting member; (c) fixing the rotational position of the pivoting member the locking means; (d) removing the first construct; and (e) placing a conjoining member of a second construct in the jig for alignment according to the fixed rotational position of the pivoting member as a head of the second construct is placed on the position of the head of the first construct on the body, the conjoining member then affixed to the head of the second construct.

The subject invention is advantageous over existing technology in that (1) the subject invention is cost effective, i.e. the subject device and/or method of use is simple in design and construction, thus reducing costs of manufacture, (2) the subject device and/or method of use is easy to use, i.e. the subject device and/or method of use essentially completes the task of trialing in three steps with no requirements for measuring angles or remembering measurements, (3) the subject invention is very compact and thus can perform trialing in an area proximate the surgical incision as opposed to transferring from/to a back table, and (4) the subject device and/or method of use is reliable, i.e. there are few moving parts to fail or loose. All of the above provides a simple, reliable, and easy to manufacture trialing system, i.e. device and/or method of use thereof.

BRIEF DESCRIPTION OF THE DRAWINGS

In the drawings:

FIG. 19 is an enlarged side sectional view of an exemplary alternative embodiment of a humeral head;

FIG. 20 is perspective view of a trialing jig for a shoulder prosthesis;

FIG. 21 is a sectional view of the trialing jig for a shoulder prosthesis of FIG. 20 taken along line 21—21 thereof;

Corresponding reference characters indicate corresponding parts throughout the several views. Like reference characters tend to indicate like parts throughout the several views.

DESCRIPTION OF THE PREFERRED EMBODIMENT(S)

Figure 1:
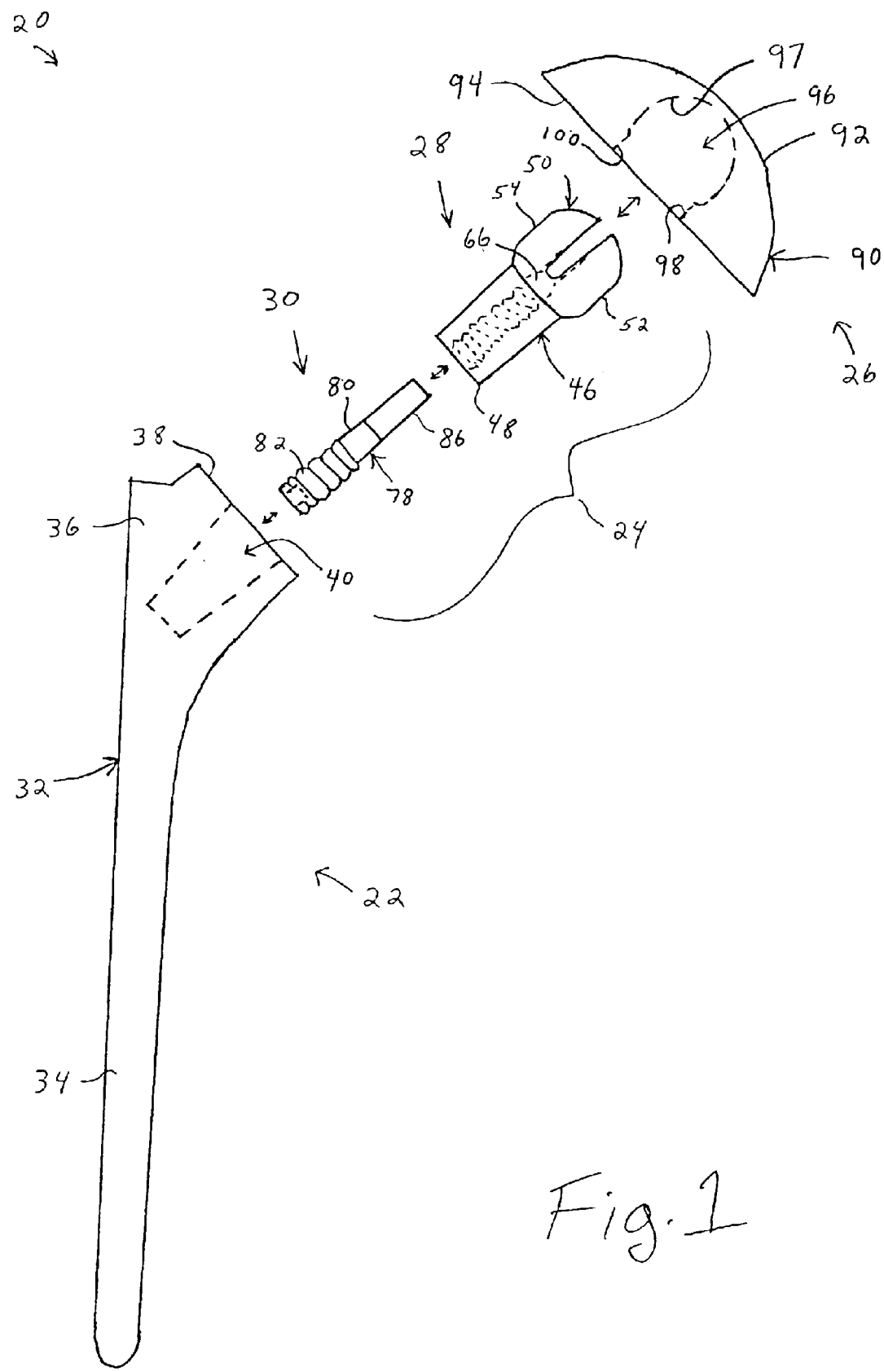
FIG. 1 is an exploded perspective view of an exemplary shoulder prosthesis incorporating the features of the subject invention in accordance with the principles thereof.

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention.

Referring now to FIG. 1 there is shown an exemplary embodiment of a shoulder prosthesis, generally designated 20. The shoulder prosthesis 20 includes a humeral component or stem 22, a conjoining and/or adjustment member or means 24, and a head 26. The head 26 is adapted, configured and/or operative to be received on the conjoining member 24 or vice versa (i.e. the conjoining member 24 is adapted, configured and/or operative to be received on the head 26) depending on the configurations of the head 26 and the conjoining member 28 and/or one's perspective. Thus, while the remaining text describes the conjoining of the head and the conjoining member, it should be appreciated that both contexts are covered thereby.

Particularly, the head 26 is adapted, configured and/or operative to be releasably affixed to the conjoining member 24. More particularly, the head 26 is adapted, configured and/or operative to be releasably locked to the conjoining member 24 in a particular or selectable rotational and/or angular orientation relative to the conjoining member 24 and/or the humeral component 22 as described further below. The conjoining member 24 is adapted, configured and/or operative to be received on the humeral component 22. Particularly, the conjoining member 24 is adapted, configured and/or operative to be releasably received on the humeral component 22. All of the components of the shoulder prosthesis 20 are manufactured from a material or materials such as are known in the art for such implants.

As depicted in FIG. 1, the conjoining member 24 includes a neck, neck member or the like 28 and a locking and/or adjustment member, screw or the like 30. The locking member 30 cooperates with the neck 28 to releasably lock or fix the head 26 in a particular orientation on the neck 28. When the conjoining member 24 is releasably disposed on the humeral component 22, the head 26 is also releasably locked or fixed with respect to the humeral component 22. As explained more fully below, the conjoining member 24 is also releasably locked or affixed to the head 26 such that the head 26 and/or the conjoining member 24 are locked against axial movement between the two.

Figure 2:
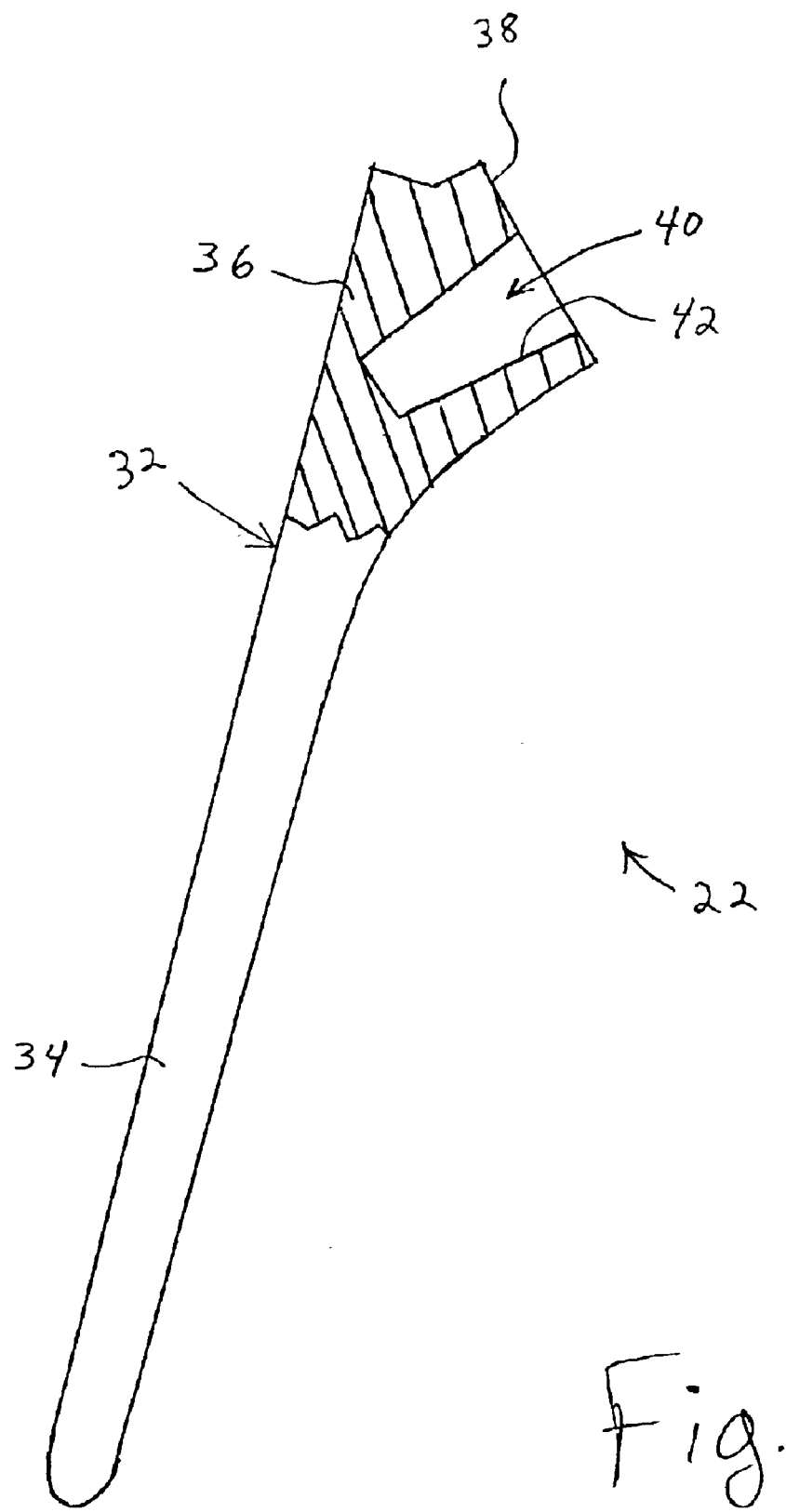
FIG. 2 is a plan and partial sectional view of the humeral component of the exemplary shoulder prosthesis of FIG. 1.

Referring now to FIG. 2, the humeral component 22 is depicted. The humeral component 22 is characterized by a body 32 having a stem or stem portion 34 and a neck or neck portion 36. The humeral component 22 may or may not have fins, collars, suture holes or the like. Therefore, such are not shown in FIG. 2. The neck 36 has a preferably substantially flat or planar surface 38 having a connector, connection or connection receptacle 40 extending therefrom into the neck 36. In one form, the connection receptacle 40 is defined by an inner wall 42. The connection receptacle 40 may be a concavity, recess, or the like. Preferably, and as shown, the connection receptacle 40 has a tapered inner wall 42. More preferably, the inner wall 42 defines a frusto-conical shaped concavity. Preferably, but not necessarily, an axis of the connection receptacle 40 is substantially perpendicular to the surface 38. The connection receptacle 40, however, may be a protuberance, boss, flange or the like (i.e. a convexity) rather than a concavity. In both cases, a mating element would be opposite (complementary) in configuration.

The humeral component 22 is adapted, configured and/or operative such that the stem 34 thereof is insertable into a humeral canal of a humerus (not shown) of a patient (not shown) after appropriate resection of the humerus. Particularly, the humeral component 22 is inserted into the humerus of the patient such that the head 36 is within the humerus and the surface 38 is substantially co-planar with a resection surface of the humerus such as is known in the art. This allows access to the connection receptacle 40 after implantation of the humeral component 22 into a humerus.

Figure 3:
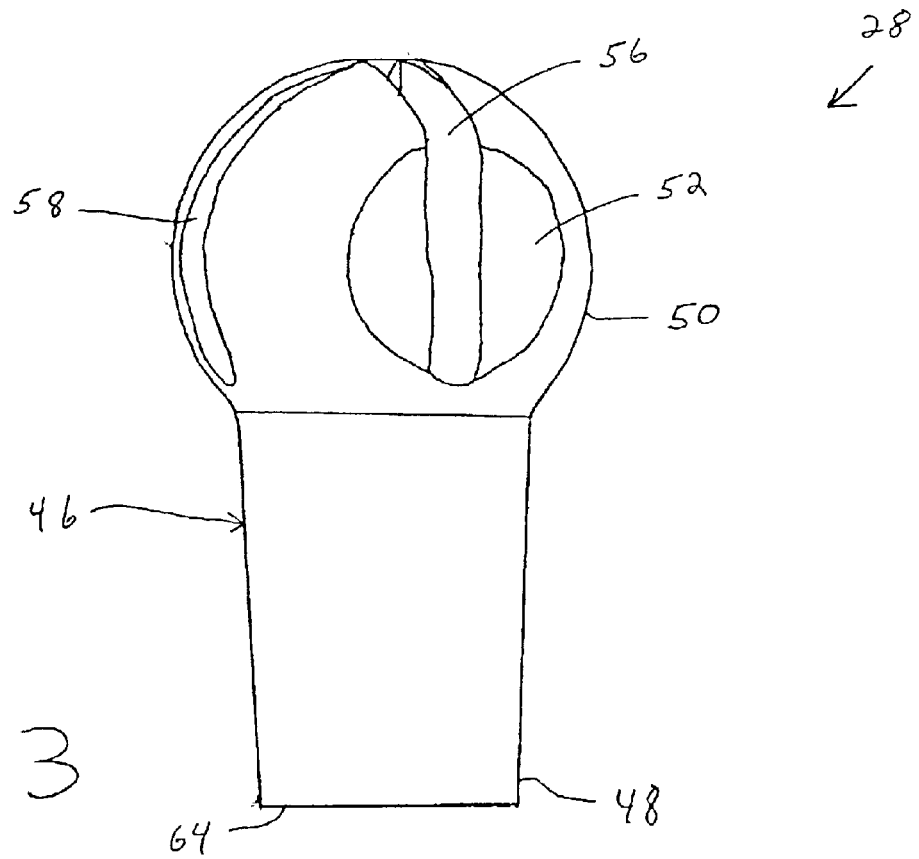
FIG. 3 is an enlarged front plan view of the neck body of the conjoining member of the exemplary shoulder prosthesis of FIG. 1.
Figure 4:
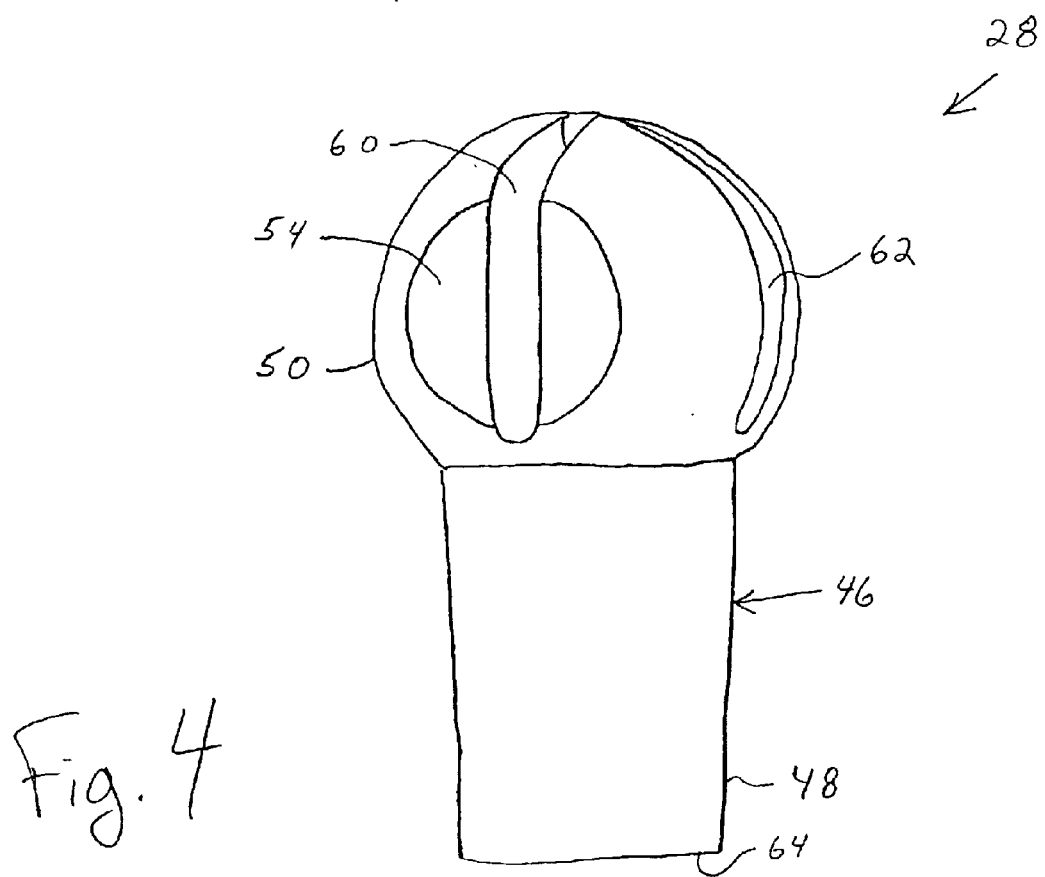
FIG. 4 is an enlarged rear plan view of the neck body of the conjoining member of the exemplary shoulder prosthesis of FIG. 3.

Referring now to FIGS. 3 and 4, the neck 28 of the conjoining member 24 is depicted. The neck 28 is characterized by a body 46 defining a first end 48 and a second end 50. In keeping with the configuration of the connection receptacle 40 as depicted in the Figures, the first end 48 is formed as a configured convexity or protuberance. In all cases, the first end 48 is configured in a complementary manner to the connection receptacle 40 of the humeral component 22, in whatever form the connection receptacle 40 may take. In the embodiment shown, the first end 48 is formed as a tapered cylinder or of a frusto-conical design.

The second end 50 is formed with a connector that may be a configured convexity or concavity. In the Figures, the second end 50 is formed as a sphere, spheroid or the like. The spheroid 50 is preferably a true sphere but may deviate therefrom and is solid except for the structures described herein. The spheroid 50 is shown with a first flat or flat portion 52 on a side thereof and a second flat or flat portion 54 that is disposed on another side thereof that is preferably, but not necessarily, diametrically opposite the first flat 52. The flats 52 and 54 preferably, but not necessarily, have the same configuration. The flats 52 and 54 form planes that are preferably, but not necessarily parallel. The planes of the flats 52 and 54 are also preferably, but not necessarily, parallel with an axial plane of the conjoining body 46. The flats 52 and 54 are disposed on the spheroid 50 such that planes defined thereby are not perpendicular to the axis of the first end 48.

While two flats are shown, it should be appreciated that the spheroid 50 may have only one flat or the spheroid 50 may have more than two flats. Furthermore, the spheroid 50 may have a key, keys, a keying structure or keying structures other than flats thereon depending on the configuration of a complementary connector, receptacle or the like of the head 26.

In a further form, the shoulder prosthesis may not have flats or any such corresponding structure. In this form, the humeral head is received onto the conjoining member 24 and fixed in angular position as described herein. Thus, it is not necessary to have flats or any such corresponding structure.

The spheroid 50 also has a first radial slit 56 (see FIG. 3) and a second radial slit 60 (see FIG. 4) that together define a continuous first radial slot. The spheroid 50 may further has a third radial slit 58 (see FIG. 3) and a fourth radial slit 62 (see FIG. 4) that together define a continuous second radial slot. In one form that is not shown, the spheroid has one continuous radial slot. This divides the spheroid into two or four portions. The spheroid 50 may have more slots than shown.

Figure 5:
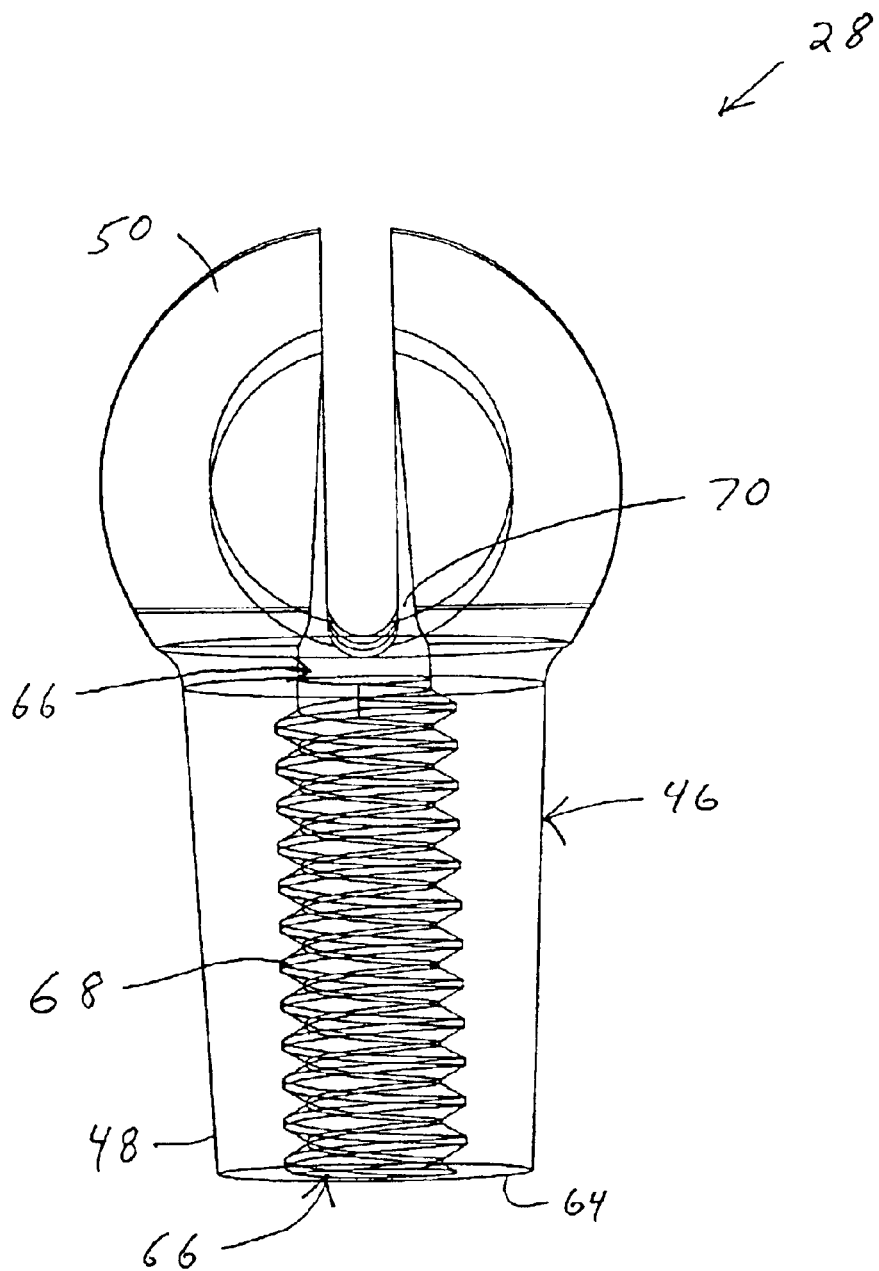
FIG. 5 is an enlarged front plan view of the neck body of FIG. 3 showing the internal structure thereof.

As best seen in FIG. 5, the neck 28 has an internal bore 66 that extends from a bottom surface 64 of the first end 48 through the interior of the second end (spheroid) 50. The bore 66 has a first portion 68 that is threaded and a second portion 70 that is tapered. Particularly, the second portion 70 is tapered in the spheroid 50, i.e. from the end of the threaded portion 68 toward the top of the spheroid 50. The second portion 70 is shaped such that the diameter reduces in a direction from the end of the first (threaded) portion 68 to the spherical end. The bore 66 is preferably, but not necessarily, concentric with the outer diameter of the first end 48.

The threaded portion 68 allows the threaded insertion and advancement of the locking screw 30. The tapered portion 70 in conjunction with the first radial slot and/or the second radial slot provides a radial spreading of the spheroid 50 (i.e. radial spreading of the portions defined by the radial slots) when the locking member 30 advances into the tapered portion 70. The spherical outer diameter is enlarged due to the expansion of the radial slots in the sphere 50 through advancement of the locking screw 30.

Figures 6, 7:
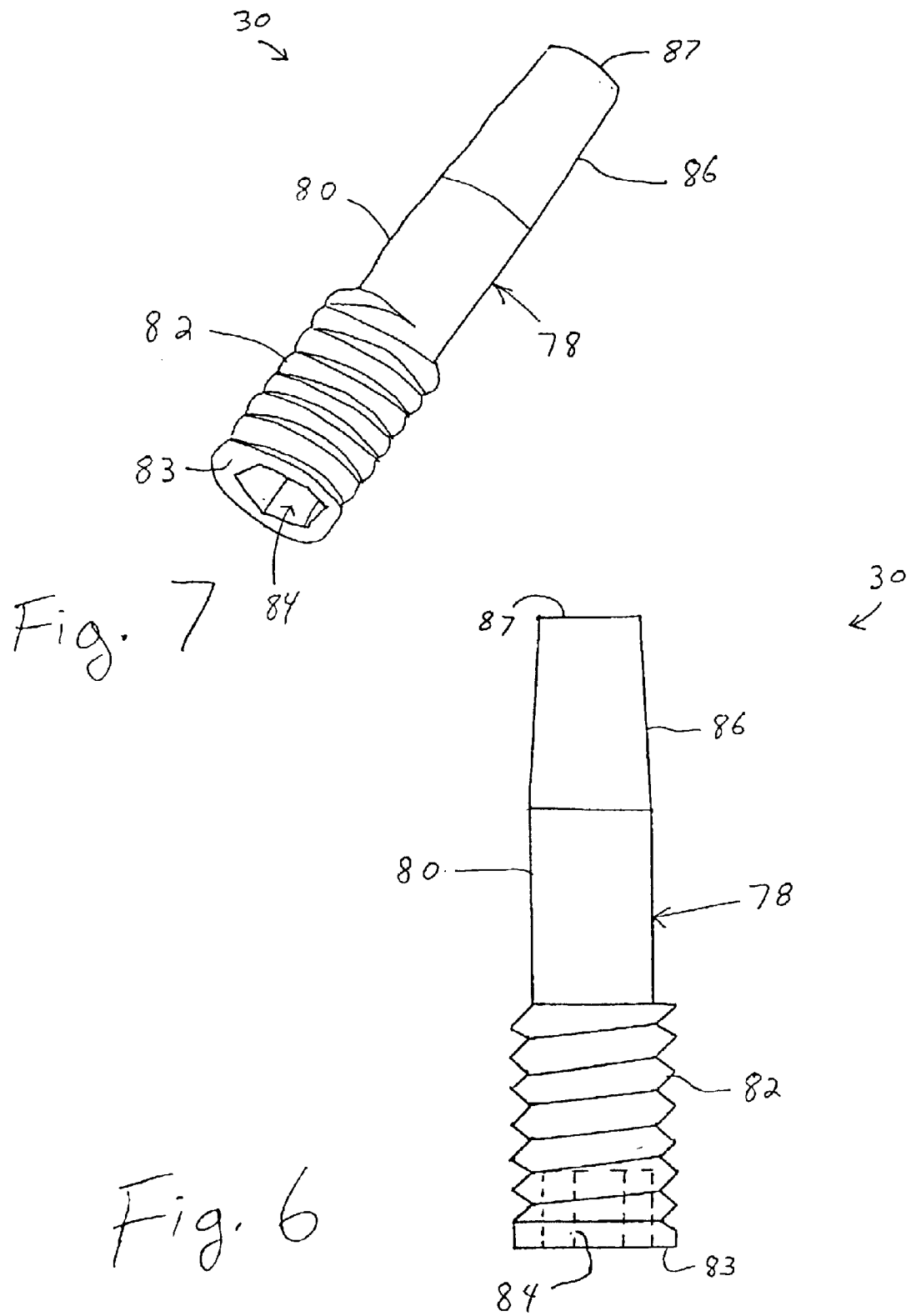
FIG. 6 is an enlarged plan view of the adjustment/locking member of the conjoining member of the exemplary shoulder prosthesis of FIG. 1.
FIG. 7 is an enlarged perspective view of the adjustment/locking member of FIG. 6.
Figure 10:
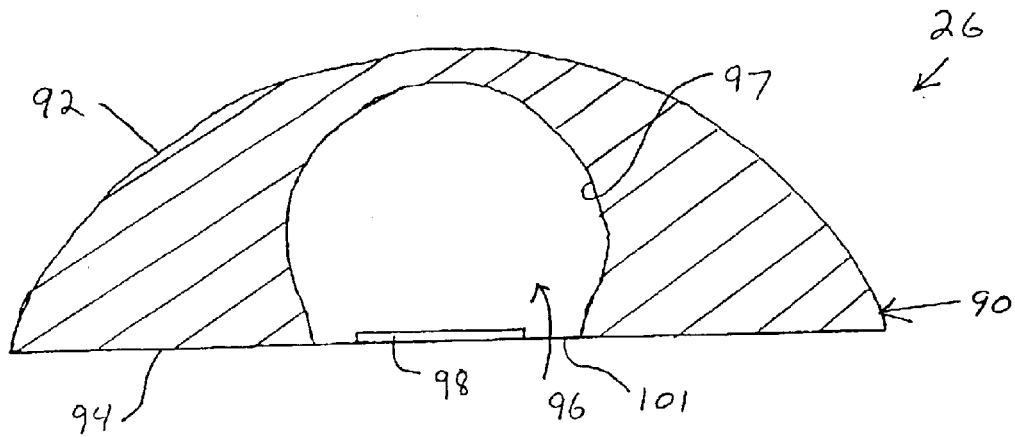
FIG. 10 is a sectional view of the head of FIG. 8 taken along line 10—10 thereof.
Figure 8:
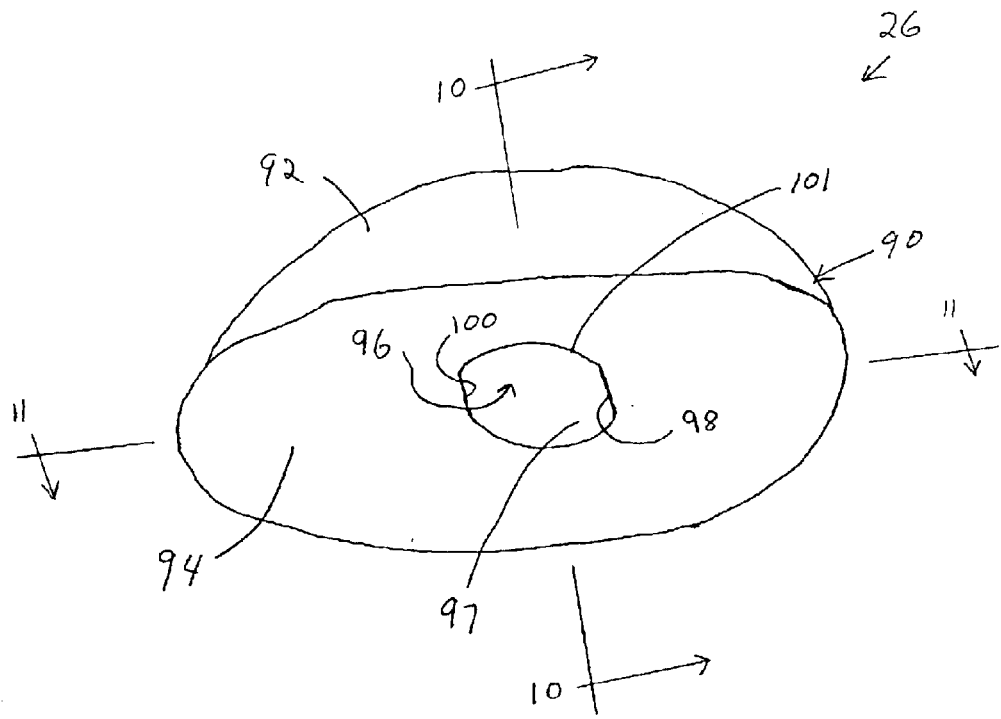
FIG. 8 is an enlarged perspective view of the head of the shoulder prosthesis of FIG. 1.
Figure 11:
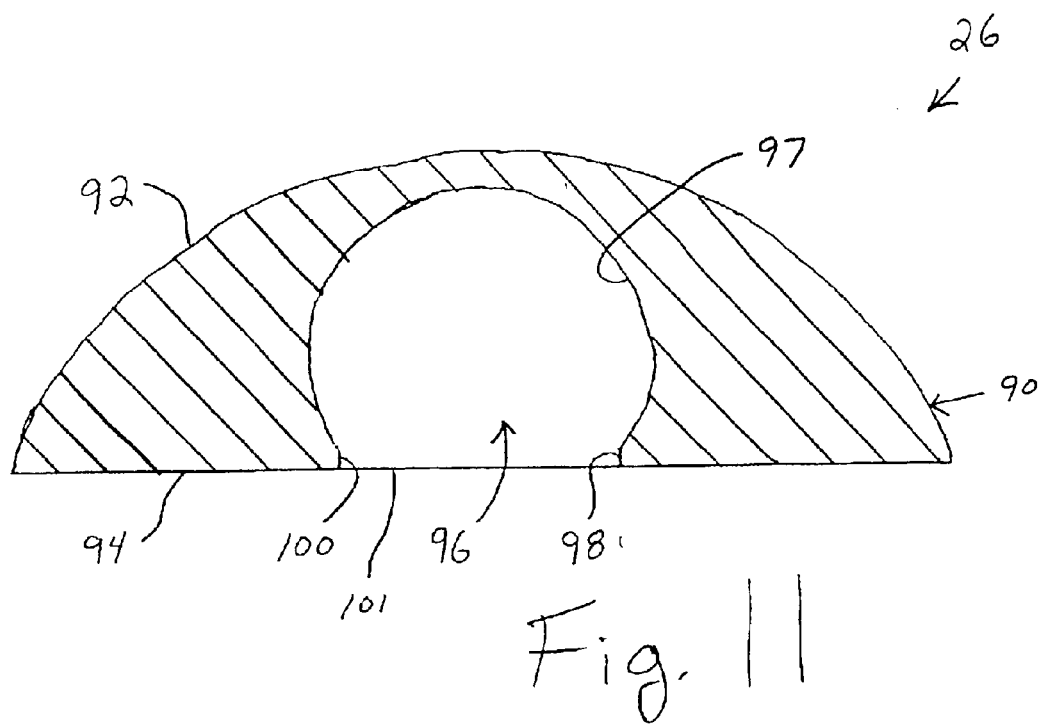
FIG. 11 is a sectional view of the head of FIG. 8 taken along line 11—11 thereof.
Figure 9:
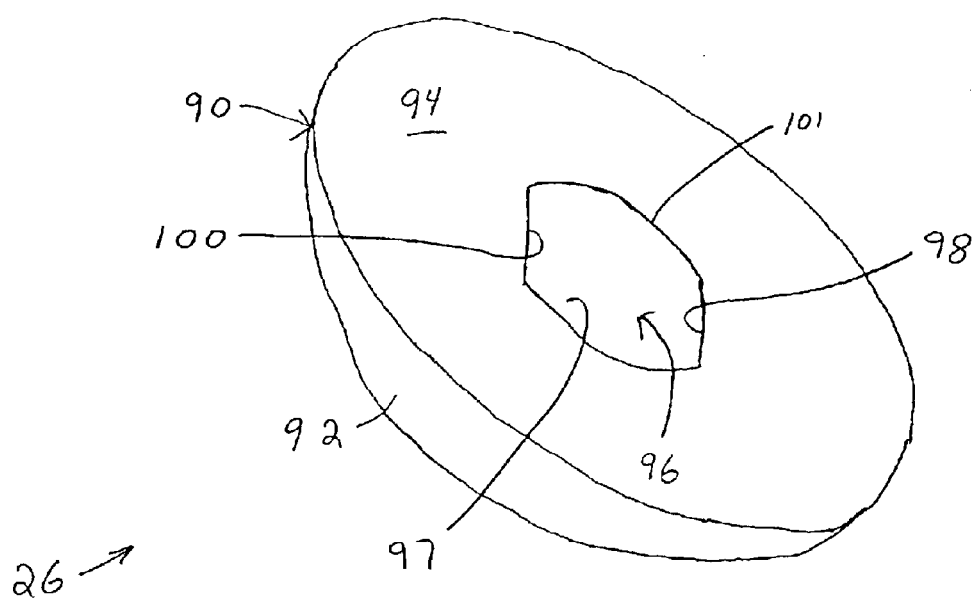
FIG. 9 is another enlarged perspective view of the head of FIG. 8 from an underside perspective.

Referring to FIGS. 6 and 7, there is depicted the locking and/or adjustment member or screw 30. The locking screw 30 is characterized by a body 78 in the general shape of a tube, cylinder, pin, rod or the like. The body 78 has a first section 80 of a generally circular outer diameter with threads 82 on one end thereof. The threads 82 are compatible with the threaded portion 68 of the bore 66 of the neck 28. The body 78 has a configured bore 84 in an end 83 thereof. The threaded bore 84 is shown configured for a hex wrench (not shown). The hex wrench is used to thread the locking member 30 into the bore 66 of the neck 28. Of course, other configurations and/or manners of advancing the locking member 30 into the neck 28.

The body 78 also includes a second portion 86 on an end of the first portion 80. The second portion 86 is tapered from a junction point to an end 87. The taper corresponds, but is larger in diameter, to the tapered portion 70 of the neck. Thus, as the second (taper) portion 86 extends into the tapered portion 70 of the bore 66, the spheroid 50 radially expands. The expansion of the spheroid 50 fixes the head 26 in its spatial orientation.

Referring to FIGS. 8–11 there is depicted the head 26. The head 26 is characterized by a body 90 formed as a general partial spheroid. Particularly, the body 90 is shaped to conform to a glenoid. The body 90 has an articulation surface 92 conforming to the general partial spheroid and a bottom surface 94. It should be appreciated that the head 26 represents any size shoulder prosthesis head. The subject invention allows the use of various sized heads with the other components of the present shoulder prosthesis 20. While a head of only one size is ultimately used for the shoulder prosthesis 20 when implanted into the patient, the components of the present shoulder prosthesis 20 allow various sized heads to be trialed and/or used when the humeral component 22 is implanted into the humerus (i.e. during and/or after the time at which the humeral component 22 is final stage implanted in the humerus). The various heads may be variously proportioned and/or sized.

The head 26 further includes a recess, cavity or the like 96 defined by an inner surface 97 within the body 90 that is open at opening 101 on the underside 94. The inner surface (wall) 97 and thus the cavity 96 is generally spheroid shape in general conformance to the spheroid head 50 of the neck 28 of the conjoining member 24. The cavity 96 is sized to receive the spheroid 50. Particularly, the cavity 96 has a diameter that is slightly greater than the diameter of the spheroid 50.

The opening 101 has a shape or configuration defining a profile. This profile can be considered in a plane defined by the underside 94. It should be appreciated that the profile of the opening 101 in the plane of the underside 94 is the same as the profile of a plane taken along the center of the spheroid 50 from flat 52 to flat 54 (or other key structure as the case may be). This allows the spheroid 50 to be keyed to the opening 101 in one rotational position.

In the present case, the profile 101 is spheroid with two flats 98 and 100. The flats 98 and 100 extend into the cavity 96 generally perpendicular to the undersurface 94. The flats 98 and 100 may extend from only approximately 2 mm or enough to provide an axial stop for the spheroid 50 against axial removal therefrom, once the spheroid 50 (member 28) is received into the cavity 96 and rotated as described herein, or may extend up to an equator of the spheroid 50. As such, other profiles or keys and thus spheroid configurations may be used. Such other configurations could include the use of dowel pins inserted from the sides of the head (with slots in the neck body). However, in the preferred embodiment, the embodiment that provides the greatest surface area of contact, thus 90° of contact at two ends, is best. While not necessary, the flats 98 and 100 are illustrated as disposed 180° or diametrically opposite one another.

It should be appreciated that the manner of releasable attachment between the conjoining member 24 and the head 26 is contemplated to and thus may vary in configuration. As an example, the cavity or receptacle in the head 26 may be fashioned or configured as a stepped bore with or without a key structure. The second end 50 of the neck 28 would thus be fashioned or configured as complementary to the stepped bore. In another example, the cavity or receptacle in the head 26 may be configured as a cone or conical shaped with or without a key structure. Again, the second end 50 of the neck 28 would thus be fashioned or configured as complementary to the cone. As yet another example, the cavity or receptacle in the head 26 may be configured as an interrupted sphere with or without a key structure. Again, the second end 50 of the neck 28 would thus be fashioned or configured as complementary to the interrupted sphere. Various combinations that allow the head to be releasably affixed or joined with the conjoining member are contemplated and thus may be used.

Figure 12:
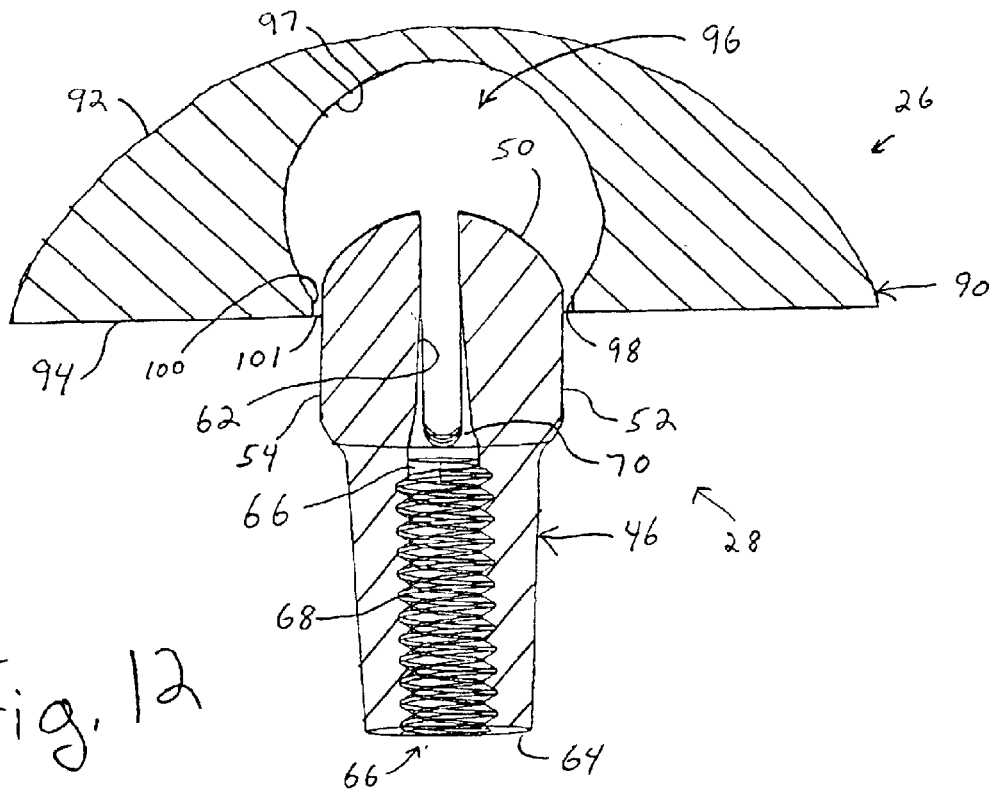
FIG. 12 is a front plan view of interaction between the head and neck illustrating a manner of conjoining in accordance with the principles of the subject invention.

The cavity 96 is configured to receive the full spheroid 50 once the spheroid 50 has been properly aligned and then inserted into the cavity 96. With respect to this feature, which releasably locks the neck 28 to the head 26, reference is made to FIGS. 12–14. FIG. 12 depicts the neck body 46 being introduced into the cavity 96 of the head body 90. Particularly, the spheroid 50 is being inserted into the cavity 96. Because of the flats 98 and 100, the spheroid 50 must be aligned such that the flats 52 and 54 of the spheroid 50 align with the flats 98 and 100 (either ones) of the opening 110. This allows the spheroid 50 to be fully received in the cavity 96 (see FIG. 13). The spheroid 50 is axially beyond the flats 98 and 100 when fully received in the cavity 96.

Figure 13:
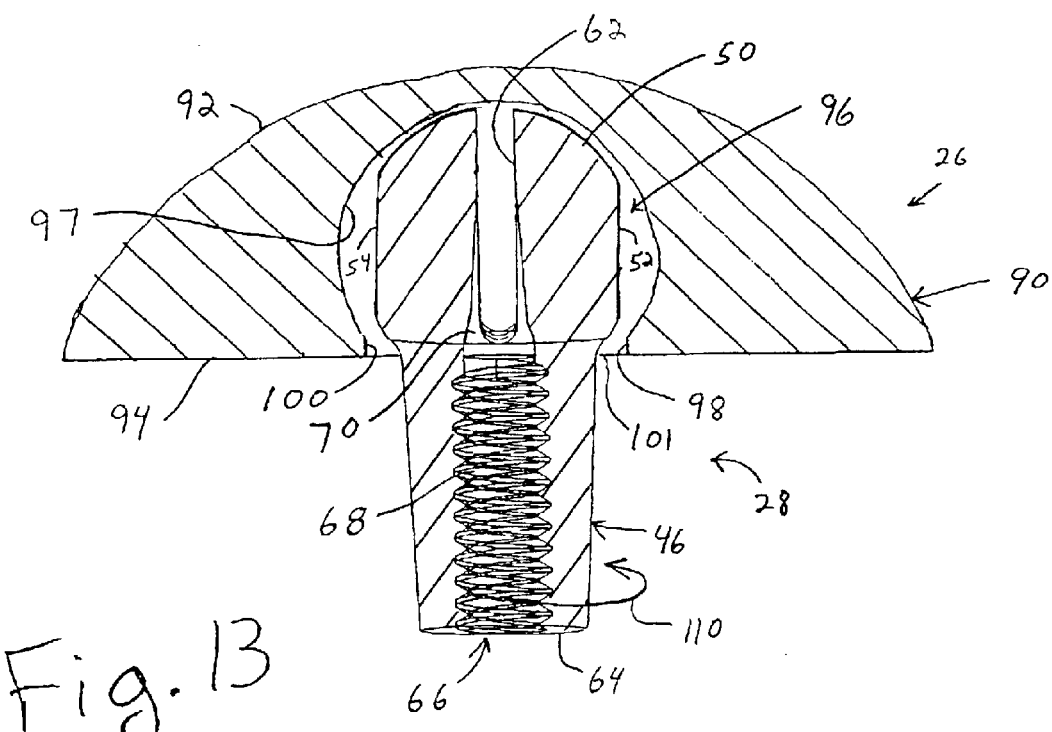
FIG. 13 is a front plan view of interaction further to the interaction of FIG. 12 between the head and neck illustrating the manner of conjoining in accordance with the principles of the subject invention.

Once the neck 28 conjoins the head 26 as depicted in FIG. 13, the neck 26 is rotated as depicted by the arrow 110. Particularly, the neck 28 is rotated a quarter turn (90°) in either direction (the arrow, however, depicting only one direction, i.e. to the right). This aligns the flats 98 and 100, and 52 and 54 at 90° relative one another (see FIG. 14 wherein only the flats 98 and 100 of the opening 110 can be seen since the flats 52 and 54 are 90° therefrom). This prevents the axial removal of the neck 28 from the cavity 96 (without 900 rotation of the neck 28 because the spheroid 50 cannot pass through the opening 110 because of the flats 98 and 100. At this point, the head is still able to rotate about two orthographic axes relative to the spheroid 50.

Figure 14:
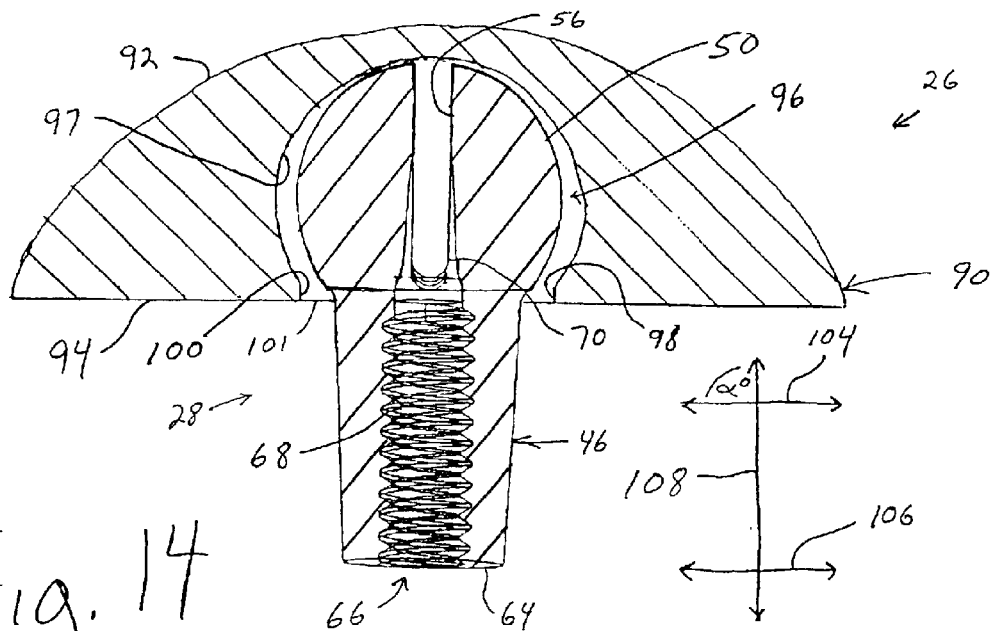
FIG. 14 is a side sectional view of the exemplary humeral head and conjoining member with the humeral head in one particular orientation.

In FIG. 14, the head (particularly the undersurface 94) defines a plane represented by the arrow 104. The neck 28 also defines a plane represented by the arrow 106. Particularly, a plane of the neck 28 is defined by a plane perpendicular to a longitudinal axis of the neck 28 taken along the bore 66 thereof. Offset of the head 26 relative to the neck 26 may be defined as an angle deviation relative to a 90° angle from the longitudinal axis of the neck 28 represented by the arrow 108. In FIG. 14, there is no offset, since the angle α is 90°.

Figure 15:
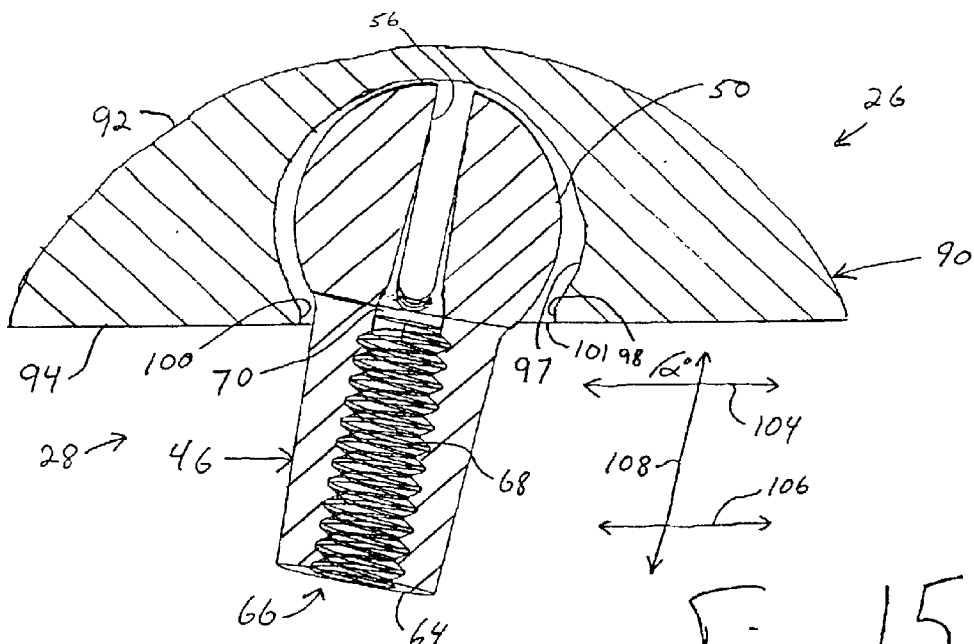
FIG. 15 is a side sectional view of the exemplary humeral head and conjoining member with the head in another particular orientation illustrating in conjunction with FIG. 14 the manner of spatial orientation of the head relative to the conjoining member and/or the humeral component.
Figure 16:
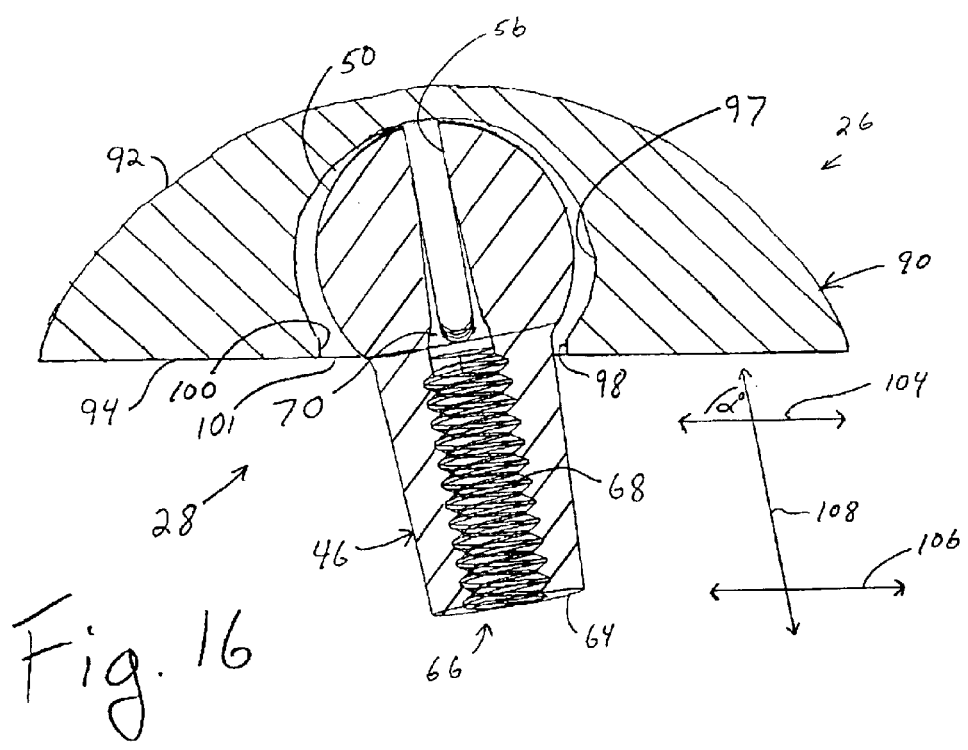
FIG. 16 is a side sectional view of the exemplary humeral head and conjoining member with the head in another particular orientation illustrating in conjunction with FIGS. 14 and 15 the manner of spatial orientation of the head relative to the conjoining member and/or the humeral component.

FIG. 15 depicts an offset of the head 26 relative to the neck 28 since the angle α is greater than 90° (i.e. the neck body 46 is angled to the left). FIG. 16 depicts an offset of the head 26 relative to the neck 28 since the angle α is less that 90° (i.e. the neck body 46 is angled to the right). The head 26 is infinitely adjustable along the two orthographic axis to set the spatial orientation of the head 26 relative to the neck 28 and thus the humeral component 22. This may be accomplished either before or after the humeral component 22 is set in the humerus of the patient.

It should be appreciated that FIGS. 14–16 only depict angular orientation relative to one axis of rotation. The other axis of rotation is orthographic to the one depicted and, while not shown, exhibits the same angular displacement in the respective spatial orientations.

Figure 17:
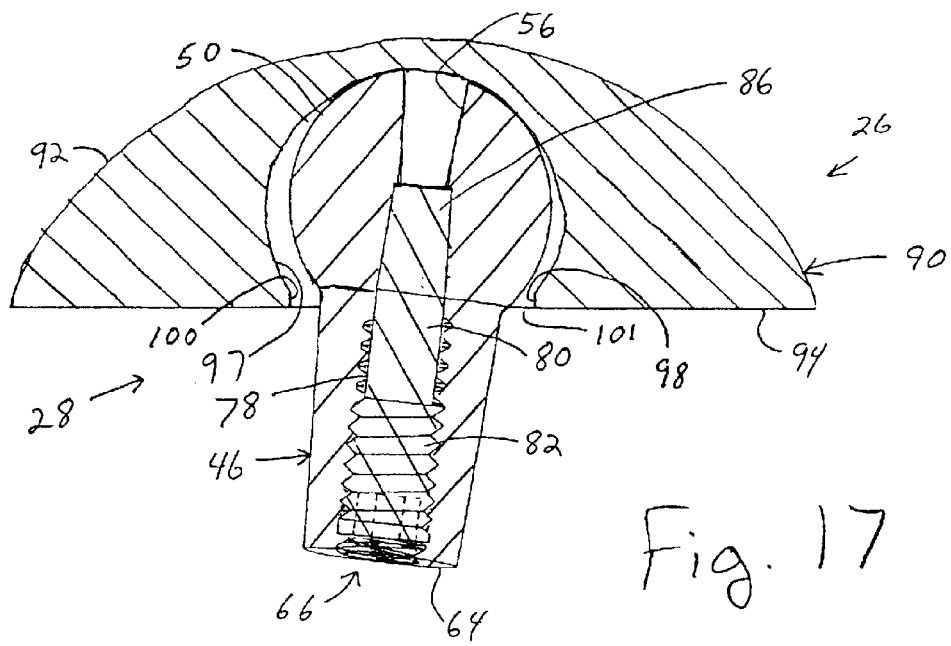
FIG. 17 is a side sectional view of the exemplary humeral head and conjoining component with the head fixed a particular orientation illustrating the manner of fixation with the locking member inserted into the neck.

Once the appropriate angular orientation of the head 26 is determined, the locking member 30 is introduced into the neck bore 66. Referring to FIG. 17, an exemplary orientation of the head 26 relative to the neck 26 is shown. The locking member or screw 30 characterized by body 78 is advanced axially into the neck body 46 by action of the mating threads. As the tapered portion 86 of the locking screw 78 enters the tapered portion 70 of the neck bore 66, the spheroid 50 is spread to expand into the cavity 96. Such radial expansion fixes the orientation of the head relative to the neck 28.

Figure 18:
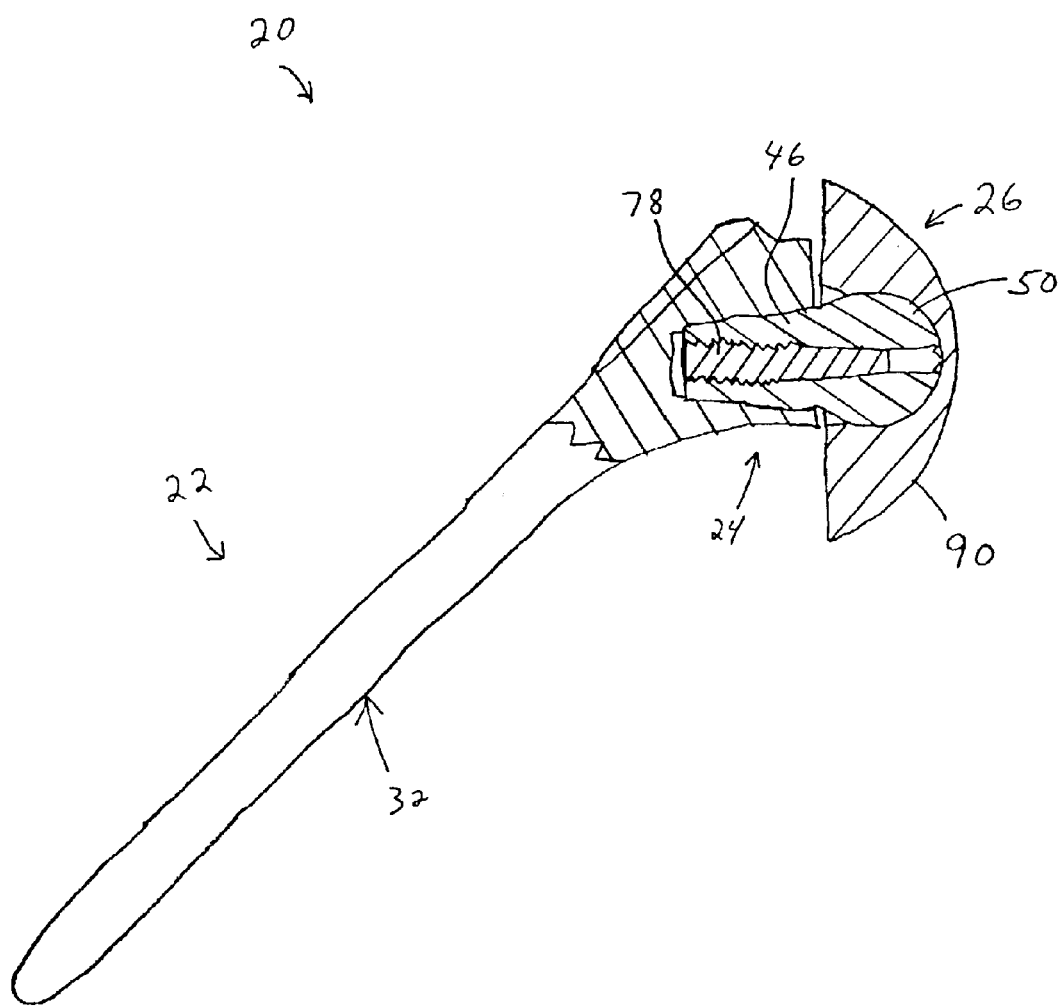
FIG. 18 is a side view of an exemplary shoulder prosthesis with a portion thereof in sectional particularly depicting the manner of assembly thereof.
Figure 31:
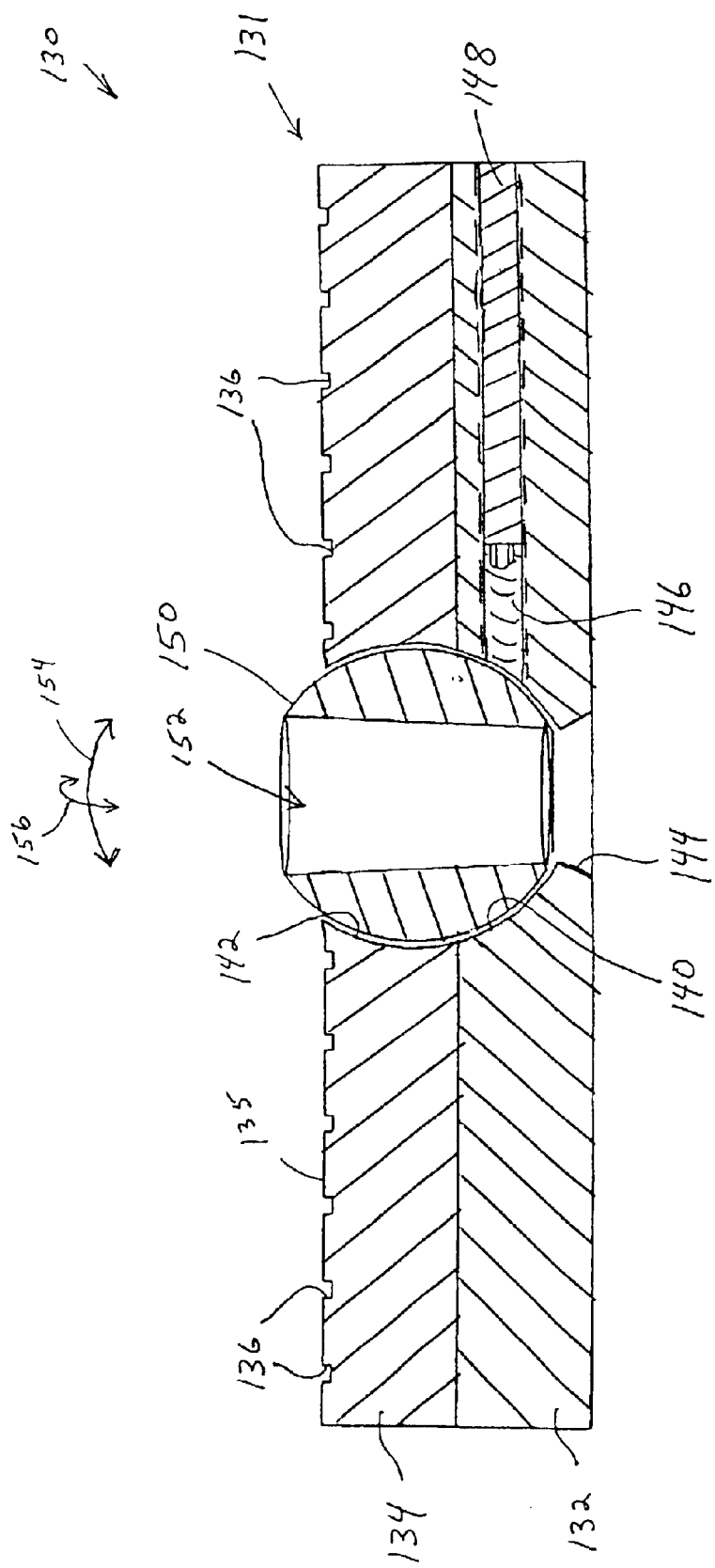

As depicted in FIG. 18, the conjoining member 24 is releasably affixed to the humeral component 22 with the head 26 releasably affixed to the conjoining member 24. The conjoining member 24 and thus the head 26 may thus be removed from the humeral component 22 especially after the humeral component 22 has already been permanently implanted into the humerus of the patient. Particularly, adjustment to the head 26 is made in vivo, making the adjustment procedure easier for a surgeon, as all landmarks for adjustment are present during the adjustment process. Further, the surgeon can cement or otherwise affix the humeral component 22 in an optimal position for fixation, and adjust humeral head position without interfering with this fixation. For example, different size heads may be tried and/or changed and spatially oriented while the humeral component 22 is implanted in the humerus.

It should be appreciated that the conjoining member 24 is releasably or removably situated on the humeral stem 22. At the same time or independent therefrom, the head 26 may be fixed on the conjoining member 24. This allows the head and locking component to be removed during preparation of the glenoid joint surface. This provides for a smoother surgical technique, possibly lowering anesthesia times, as well as provide other advantages. The subject configuration also allows retrofit of a new head (with a conjoining component) onto a previously implanted shoulder prosthesis in need of revision.

Referring now to FIG. 19, there is depicted an exemplary alternative embodiment of a humeral head, generally designated 26'. The head 26' may be used in any situation where the head 26 described above may be used. The head 26' also functions in the same manner as the head 26. Additionally, the humeral head 26' may come in various sizes. In accordance with an aspect of the subject invention, the configuration of the humeral head 26' allows an alignment system as described herein to be used.

The head 26' is defined by a body 90' in like manner to the body 90 of the head 26. The body 90' includes an articulation surface 92' again in like manner to the articulation surface 92 of the body 90. The body 90' has an interior spheroid cavity 96' defined by a spheroid wall or surface 97'. A bore 122 is defined in an apex of the articulation surface 92'. The bore 122 provides communication between the cavity 96' and outside of the articulation surface 92'. The bore 122 further is preferably, but not necessarily tapered. In the exemplary embodiment of the head 26', the tapered bore 122 tapers from the spherical cavity 96' to the articulation surface 92'.

The body 90' further includes an inner and annular groove 120. The annular groove 120 extends an axial distance into the body 90'. An opening 101', providing communication with the cavity 96', begins from a plane defined at an annular axial end of the annular groove 120. One 98' of two flats is shown, the other of which is disposed diametrically opposite the flat 98' and thus not seen in the view of FIG. 19, that extend from the opening profile 101' axially into the cavity 96'. The flats function in the same manner as the flats 98 and 100 described herein. The cavity 96' is sized to receive an appropriate spheroid end of a neck of a conjoining component. Using this embodiment, a hex (or other configuration) on the locking screw can be on the tapered end thereof, thus allowing a hex (or other appropriate shaped) driver to actuate the locking screw through the head instead of from the underside of the head.

The head 26' also includes a first and second cutout of which only one cutout 124 can be seen in FIG. 19. The other cutout is disposed diametrically opposite the cutout 124. The cutouts are utilized for alignment when used with a trialing jig as described below. It should be appreciated that the cutouts may instead be marks or markings on the humeral head 26' or other similar features.

Referring now to FIG. 20, there is depicted an exemplary embodiment of a trialing jig, jig or the like, generally designated 130 that may be used with the subject shoulder prosthesis 20. The jig 130 may also be used on shoulder prostheses other than those described herein. The jig 130 is configured to spatially position or orient a humeral head relative to a conjoining member or vice versa. It should be appreciated that the jig 130 represents one particular embodiment the general principles of which are described below along with alternative components.

Particularly, the trialing jig or jig 130 is used to spatially position the humeral head 26 on the neck 28 of the conjoining member 24 and translate the spatial positioning to a final implant construct (i.e. a humeral head and a neck or e.g. conjoining component/member 24). This may be accomplished after the humeral component 22 has been implanted into a resected humerus. The jig 130 consists of a retention body (body) having or retaining a rotatable, rotational, pivotable or pivoting member that may or may not include an external lock or locking mechanism or member. One such jig is exemplified in FIG. 20.

Particularly, in FIG. 20, the body is embodied as a plate 131. The plate 131 is here comprised of a first or lower plate 132 and a second or upper plate 134 although the plate 131 may be a single plate. The first (lower) and second (upper) plates 132 and 134 are joined such that inner surfaces thereof are joined and fixed. The first and second plates 132 and 134 together define a cavity 138 therein., The cavity 138 is shown as a sphere or spheroid. However, it should be appreciated that the cavity 138 may be formed into another shape that allows a same shaped member to rotate or pivot therein about or in at least two axes. These axes can be orthographic or polar. For example, one can achieve the same angular movement by rotating about an axis perpendicular to a plane of the plate (body) and any axis that lies within the plane of the plate. In a single body embodiment, the retention body would have a cavity formed therein. Particularly, the first plate 132 has a first sphere portion or spherical hole 140 cut out therefrom, while the second plate 134 has a second sphere portion or spherical hole 142 cut out therefrom. The first and second sphere portions 140 and 142 together define the sphere or spheroid 138. Preferably, the first and second sphere portions 140 and 142 are each half spheres or spheroids.

The first plate 132 also includes a tapered bore 144 that is in communication with the first sphere portion 140 and thus the bottom of the sphere 138. Additionally, the body 131 may have a retention or locking mechanism. In one form, and as shown in the Figures, the retention or locking mechanism includes a threaded bore 146 that extends from an outside surface of the body (plate 131) to the sphere 138 (i.e. the surface defining the sphere 138). Particularly, as shown, the threaded bore 146 extends from an outside surface of the first plate 132 to the surface of the first sphere portion 140. The threaded bore 146 is adapted to receive a threaded set screw or the like. It should be appreciated that while the threaded bore 146 is shown in the first or lower plate 132, the threaded bore 146 may be disposed in the second or upper plate 134. Also, the orientation of the threaded screw bore 146 may be varied appropriately.

Rather than a set screw as described above, a retention or locking mechanism such as a spring-loaded cam mechanism actuated by a lever, may be used as described herein. It should be appreciated that other types of retention mechanisms may also be used.

The plate 131 has alignment marks or markings that are embodied as grooves or etched lines 136. The grooves 136 are parallel to one another and provide alignment demarcations for the humeral head 26 with respect to the neck 28. The grooves 136 are disposed on an upper surface of the second plate 134 and run from one side thereof to another side thereof. These lines could also form a grid such as a Cartesian or polar grid. Furthermore, there could be a series of machined holes or detents. The device could also provide incremental detents that fit with a protrusion in the head. In this manner, there could be precise replication of head rotation with an orientation angle transfer being accomplished in specific increments.

Referring to FIG. 21, the jig 130 is depicted with various jig components situated therein and/or thereon. It should be appreciated that the jig 130 is shown in FIG. 21 in sectional view taken along line 21—21 of FIG. 20. However, a set screw or the like 148 is shown disposed in the threaded bore 146. Rotation of the set screw 148 in one direction advances the set screw 148 toward the sphere 142, while rotation of the set screw 148 in an opposite direction withdraws the set screw 148. Also shown in FIG. 21 which is not depicted in FIG. 20 is a sphere 150. The sphere 150 is disposed in the spherical hole or opening 142. The sphere 150 is sized to closely fit the spherical hole 142 such that the sphere 150 can freely rotate within the spherical hole 142 but which cannot translate therein (i.e. relative to the plate 131). The sphere 150 is rotatable about at least two (2) axes that are perpendicular and extend through a center of the sphere 150. The sphere 150, however, cannot translate within or with respect to the body 131.

The sphere 150 includes a bore 152 that is configured in like manner (but slightly larger) than the neck body 46 (of the shoulder prosthesis 20) in order to receive a neck body 46 therein. Particularly, the bore 152 is tapered to receive the tapered neck body 46. The bore 152 has an axis running through the center of the sphere 150. The sphere 150 is able to rotate in various axes as represented by the arrows 154 and 156. The set screw 148 is able to lock rotation of the sphere 150 by contact therewith, particularly via advancement of the set screw 148.

It should be appreciated that the "sphere" 150 may be any shape to conform to or with the shape of the cavity 138. Depending on the shape of the rotating member and tolerances between the rotating member and the cavity, a retention or locking mechanism may not be necessary. The rotating member may fit with enough tolerance to be rotated or pivoted, but not freely.

Figure 23:
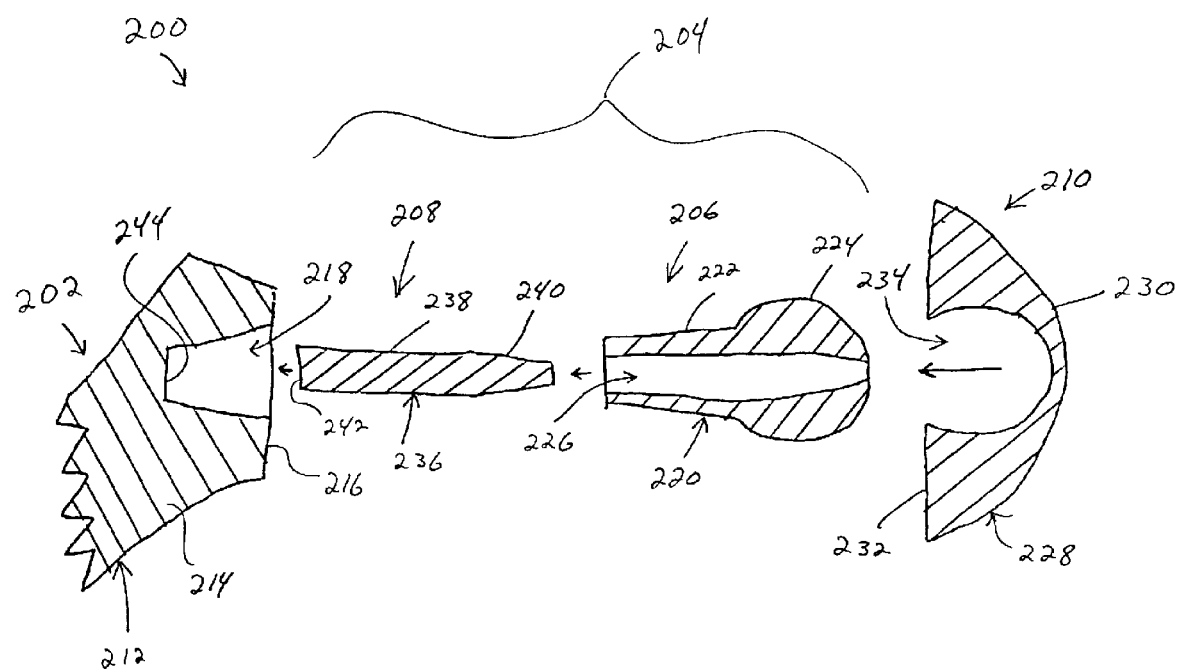
FIG. 23 is an exploded sectional view of a further exemplary alternative embodiment of a shoulder prosthesis in accordance with the principles of the subject invention.

Referring now to FIG. 23, there is depicted another exemplary embodiment of a shoulder prosthesis, generally designated 200, in accordance with the principles of the subject invention. The shoulder prosthesis 200 includes a humeral component or stem 202, a conjoining member or structure 204, and a humeral head 210.

The humeral component 202 (of which only a portion thereof is shown in FIG. 23) includes a body 212 having a head 214 and stem (not shown). The head 214 has a surface 216 in which is situated a concavity 218. The concavity 218 is configured in a manner to receive a component of the conjoining member 204. Preferably, the concavity 218 is a tapered concavity and, more particularly is a Morse taper concavity.

The humeral head 210 is characterized by a body 228 having an articulation surface 230 and an underside or undersurface 232. In FIG. 23, the body 228 includes a concavity 234 of a particular configuration. It should be appreciated in like manner to the other embodiments described herein, that the concavity 234 may alternatively be a convexity of a particular configuration. In FIG. 23, the concavity 234 is configured as a sphere or spheroid. Other configurations may be used for the concavity or convexity of the head 210.

The conjoining member 204 includes a neck member 206 and a locking pin 208. The neck member 206 is characterized by a body 220 having a tapered portion 222 and a convexity 224. The tapered portion 222 is configured in a substantially complementary manner to the concavity 218 of the humeral component 202 for releasable mating (releasable fixation) therewith in a manner as described above in conjunction with the other embodiments. The convexity 224 is of a particular configuration to releasably mate with the concavity 234 of the head 210. It should be appreciated in like manner to the other embodiments described herein, that the convexity 224 may alternatively be a concavity of a particular configuration. In FIG. 23, the convexity 224 is configured as a sphere or spheroid. The sphere 224 preferably includes slots in like manner to the other shoulder prostheses described herein. Other configurations may be used for the concavity or convexity of the neck 206. The neck 206 also includes a tapered bore 226 extending therethrough for receiving the pin 208. The convexity/concavity 224 of the conjoining neck 220 is adapted to releasably join or mate with the concavity/convexity 234 of the head 210.

The pin 208 is characterized by a body 236 having a cylindrical end 238 and a tapered end 240. The pin 208 is oversized in length with respect to the neck 206, but is sized to be received in the bore 226 of the neck 206. The tapered end 240 of the pin 208 spreads the spheroid 224 in like manner to that shown and described above with respect to the other embodiments.

In use, the head 210 is positioned appropriately on the neck 206. The lock pin 208 is then situated into the bore 226 of the neck 206. The construct (head 210 and conjoining member 204 is then situated on the humeral component 202. When the end 242 of the pin 208 bottoms out (contacts) end 244 of the cavity 218, the pin 208 is advanced through the conjoining (neck) member 206. Impaction of the head 210 then seats the lock pin taper 240 in the mating taper of the convexity 224 thereby securing the head 210 onto the conjoining member 206. In this embodiment, threads are eliminated in both the pin and neck of the conjoining member 204.

Use of the Jig

It should be appreciated that the jig 130 is adapted for use with the shoulder prosthesis 20. Particularly, the jig 130 is adapted for use with the conjoining member 24 and the head 26 as described herein.

Figure 22:
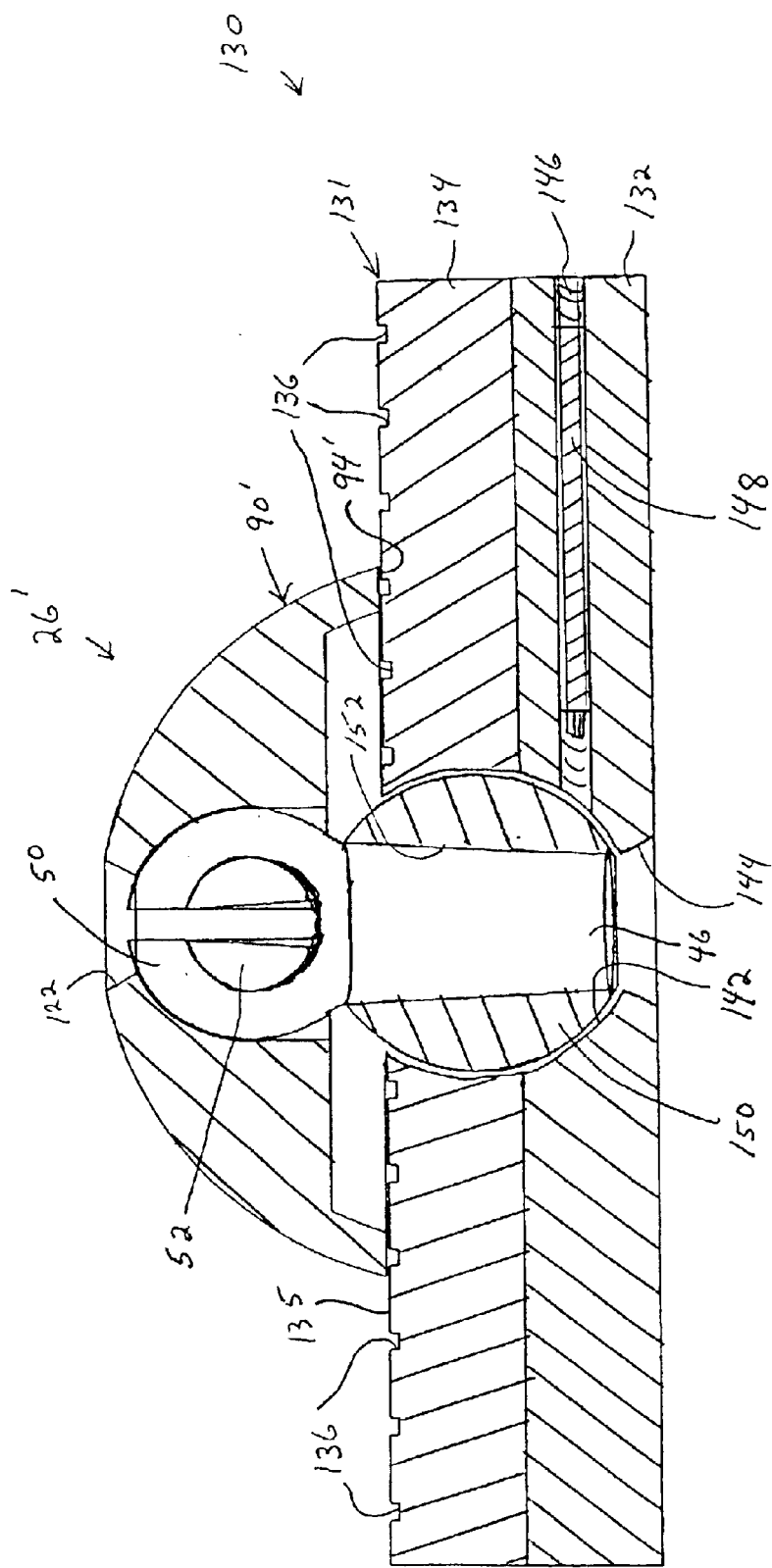
FIG. 22 is a sectional view of the trialing jig of FIG. 20 in like manner to FIG. 21, particularly depicting a conjoining component being trialed on a humeral head in accordance with the principles of the subject invention.

Referring additionally to FIG. 22, an exemplary manner of use of the jig 130 will be described. It should be appreciated that an implant construct is made of a humeral head and a neck. As described above, the implant construct allows rotational movement between the head and the neck wherein the neck may be considered as movable relative to the head or the head may be movable relative to the neck. In either case, the positioning or orientation of the two components (i.e. the head and neck) may is releasably lockable as provided herein. Further, there is typically a trial implant construct and a final implant construct.

A trial implant construct is presented to the jig 130 in a locked position, meaning that the neck 46 is locked relative to the head 26'. The trial implant construct is used to vary the position of the head 26 after the humeral component 22 has been implanted in the humerus. The trail implant is thus used to obtain an appropriate spatial positioning of the head. This spatial positioning is then transferred to a final implant construct with the aid of the present jig 130. Particularly, as shown in FIG. 22, the neck 46 is inserted into the bore 152 of the sphere 150. The sphere 150 is free to rotate within the spherical hole 142. Once the neck 46 is within the bore 152 of the sphere 150, the trial implant construct is positioned through movement of the sphere 150 such that the flat side (undersurface 94') of the head 26' is flush with the upper surface 135 of the plate 131. Particularly, when the tapered neck 46 is positioned in the sphere 150 and the head 26' is positioned with its bottom surface 94' flush with the upper surface 135, the sphere 150 rotates appropriately. The head 26 is rotated until the alignment marks on the head 26 align with the alignment marks 136 on the jig 130.

Once the head is properly aligned on the jig 130, the set screw 148 is advanced toward the sphere 150 to lock the sphere 150 from rotation. The trial implant construct is then removed from the jig 130. This leaves the sphere 150 in a locked reference position for transferring the spatial positioning of the head (i.e. spatial positioning of the head and neck) to a final implant.

The final implant construct is then placed in the jig in a loose state. Particularly, the neck 46 of the final implant construct is placed in the bore 152 of the locked sphere 150, with the head 26 positioned on the neck 46, but not locked thereto. Once the flat side 94 of the head 26 is flush against the upper surface 135 of the plate 131 and the alignment mark or marks on the head 26 are properly aligned with the alignment mark or marks of the plate 135, the head 26 may be fixed in spatial position relative to the neck 46 as described herein. The final implant construct may then be removed from the jig 130 and implanted onto the humeral component 22.

There is a plurality of advantages of the subject invention arising from the various features of the shoulder prosthesis head alignment jig described herein. It will be noted that alternative embodiments of the shoulder prosthesis head alignment jig of the subject invention may not include all of the features described yet still benefit from at least some of the advantages of such features. Those of ordinary skill in the art may readily devise their own implementations of a shoulder prosthesis head alignment jig that incorporate one or more of the features of the subject invention and fall within the sprit and scope of the subject invention.

What is claimed is:

1. A jig for transferring spatial positioning of a humeral head of a first construct relative to a conjoining member of the first construct to a second construct having a humeral head and conjoining member, the jig comprising:
    a body defining a flat surface;
    a cavity within said body;
    a pivoting member disposed within said cavity, said pivoting member having a configured bore accessible through said body and adapted to freely pivot within said cavity; and
    locking means situated in said body and adapted to selectively engage said pivoting member to releasably fix a rotational position of said pivoting member;
    wherein said configured bore is adapted to receive a conjoining member of the first construct and orient said conjoining member relative to a position of the head on said flat surface of said body via pivoting of said pivoting member, said locking means releasably fixing rotational position of said pivoting member during which the first construct is removed and a conjoining member of a second construct is placed therein for alignment according to the fixed rotational position of said pivoting member as a head of the second construct is placed on the position of the head of the first construct on said body, the conjoining member then affixed to the head of the second construct.

2. The jig of claim 1, wherein said body comprises a plate.

3. The jig of claim 2, wherein said plate comprises a first plate having a first portion and a second plate having a second portion, the first and second portions defining said cavity.

4. The jig of claim 1, wherein said body further includes a plurality of alignment markings on a surface of said body.

5. The jig of claim 4, wherein said plurality of alignment markings comprises grooves on an upper surface of said body.

6. The jig of claim 1, wherein said locking means comprises a set screw.

7. The jig of claim 6, wherein said set screw is threaded and said body further includes a threaded set screw bore extending from an outside surface of said body to said cavity.

8. A jig for transferring spatial orientation of a humeral head to a conjoining member of a first construct to a humeral head and conjoining member of a second construct, the jig comprising:
    a body having an upper surface, a spherical cavity, and an opening in said upper surface;
    a sphere disposed in said spherical cavity and having a bore configured to receive a neck of a first construct, said sphere adapted to freely rotate within said spherical cavity and without translation relative to said body; and
    locking means situated in said body and adapted to selectively engage said sphere to releasably fix a rotational position of said sphere;
    wherein said configured bore is adapted to receive a neck of the first construct and orient said neck relative to a position of the head on said flat surface of said body via rotation of said sphere, said locking means releasably fixing rotational position of said sphere during which the first construct is removed and a neck of a second construct is placed therein for alignment according to the fixed rotational position of said sphere as a head of the second construct is placed on the position of the head of the first construct on said body, the neck then affixed to the head of the second implant construct.

9. The jig of claim 8, wherein said body comprises a plate.

10. The jig of claim 9, wherein said plate comprises a first plate having a first spherical portion and a second plate having a second spherical portion, the first and second spherical portions defining said spherical cavity.

11. The jig of claim 8, wherein said body further includes a plurality of alignment markings on an outside surface thereof.

12. The jig of claim 11, wherein said plurality of alignment markings comprises grooves.

13. The jig of claim 8, wherein said locking means comprises a set screw.

14. The jig of claim 13, wherein said set screw is threaded and said body further includes a threaded set screw bore extending from an outside surface of said body to said spherical cavity.

15. A method of transferring spatial orientation of a first construct having a humeral head adapted to be releasably affixed to a conjoining member to a second construct having a humeral head adapted to be releasably affixed to a conjoining member, the method comprising the steps of:
    fixing a spatial orientation of a humeral head relative to a conjoining member of a first construct;
    placing the conjoining member of the first construct into a jig, the jig comprising:
        a body defining a flat surface;
        a cavity within said body;
        a pivoting member disposed within said cavity, said pivoting member having a configured bore and adapted to freely rotate within said cavity; and
        locking means situated in said body and adapted to selectively engage said pivoting member to releasably fix a rotational position of said pivoting member;
        wherein said configured bore is adapted to receive a conjoining member of the first construct and orient said conjoining member relative to a position of the head on said flat surface of said body via rotation of said pivoting member;

fixing the rotational position of said pivoting member the locking means;

removing the first construct; and placing a conjoining member of a second construct in the jig for alignment according to the fixed rotational position of said pivoting member as a head of the second construct is placed on the position of the head of the first construct on said body, the conjoining member then affixed to the head of the second construct.

* * * * *